United States Patent
Razzetti et al.

(10) Patent No.: US 10,752,654 B2
(45) Date of Patent: Aug. 25, 2020

(54) METHOD FOR PREPARING A FARNESOID X RECEPTOR AGONIST

(71) Applicant: DIPHARMA FRANCIS S.r.l., Baranzate (IT)

(72) Inventors: Gabriele Razzetti, Baranzate (IT); Anna Iuliano, Baranzate (IT); Luca Giannotti, Baranzate (IT); Grazia Iannucci, Baranzate (IT); Emanuele Attolino, Baranzate (IT); Vittorio Lucchini, Baranzate (IT); Renzo Graziosi, Baranzate (IT)

(73) Assignee: Dipharma Francis S.R.L., Baranzate (MI) (IT)

( * ) Notice: Subject to any disclaimer, the term of this patent is extended or adjusted under 35 U.S.C. 154(b) by 0 days.

(21) Appl. No.: 16/090,853

(22) PCT Filed: Apr. 3, 2017

(86) PCT No.: PCT/EP2017/057868
§ 371 (c)(1),
(2) Date: Oct. 3, 2018

(87) PCT Pub. No.: WO2017/174515
PCT Pub. Date: Oct. 12, 2017

(65) Prior Publication Data
US 2019/0106455 A1  Apr. 11, 2019

(30) Foreign Application Priority Data

Apr. 4, 2016 (IT) .................. 102016000034216
Nov. 16, 2016 (IT) .................. 102016000115948

(51) Int. Cl.
*C07J 9/00* (2006.01)
*C07J 21/00* (2006.01)

(52) U.S. Cl.
CPC ............. *C07J 9/005* (2013.01); *C07J 21/006* (2013.01)

(58) Field of Classification Search
CPC .................. C07J 9/005; C07J 21/006
See application file for complete search history.

(56) References Cited

FOREIGN PATENT DOCUMENTS

| CN | 105 315 320 A | 2/2016 |
| CN | 105 777 835 A | 7/2016 |
| WO | 2002/072598 A1 | 9/2002 |

OTHER PUBLICATIONS

Sepe et al., Conicasterol E, a Small Heterodimer Partner Sparing Farnesoid X Receptor Modulator Endowed with a Pregnane X Receptor Agonistic Activity, from the Marine Sponge Theonella swinhoei, J. Med. Chem. 2012, 55, 84-93.
Zhou et al., "Stereocontrolled Conversion of Hyodeoxycholic Acid into Chenodeoxycholic Acid and Ursodeoxycholic Acid", J. Chem. Soc. Perkin Trans. 1990, 1-3.
Gobbini et al., "Novel analogues of Istaroxime, a potent inhibitor of Na+,K+-ATPase: Synthesis, structure-activity relationship and 3D-quantitative structure-activity relationship of derivatives at position 6 on the androstane scaffold", Bioorg. Med. Chem., 2010, 4275-4299.
Drefahl et al., "Synthesen von Alkyliden-Steroiden durch Wittig-Reaktion", Chem. Ber. 1965, 98, 604-612.
Drefahl et al., "Synthesis of Alkylidene-Steroids by Wittig-Reaction, Institute for Organic Chemistry and Biochemistry" 1965, 98, 604-612 (Translation).

*Primary Examiner* — Timothy R Rozof
(74) *Attorney, Agent, or Firm* — Rothwell, Figg, Ernst & Manbeck, P.C.

(57) ABSTRACT

The invention relates to a process for preparing a compound of formula (I)

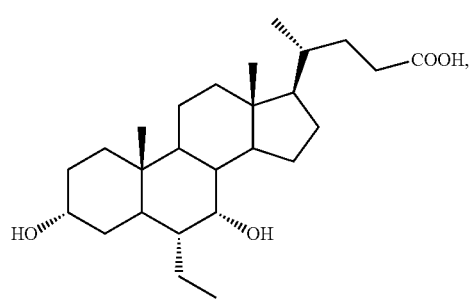

in particular obeticholic acid and intermediates suitable for its synthesis.

13 Claims, No Drawings

METHOD FOR PREPARING A FARNESOID X RECEPTOR AGONIST

CROSS REFERENCE TO RELATED APPLICATION

This application is a 35 U.S.C. 371 National Phase Entry Application from PCT/EP2017/057868, filed Apr. 3, 2017, which claims the benefit of Italian Patent Application Nos. 102016000034216 filed Apr. 4, 2016 and 102016000115948 filed on Nov. 16, 2016, the disclosure of which are incorporated herein in their entirety by reference.

FIELD OF THE INVENTION

The present invention relates to hyodeoxycholic acid and its intermediates, in particular to their use in a process for preparing obeticholic acid.

STATE OF THE ART

6α-Ethyl-3α,7α-dihydroxy-5β-cholan-24-oic acid, also known as 6α-ethyl-chenodeoxycholic acid, obeticholic acid or as 6-ECDCA, having formula (Ia),

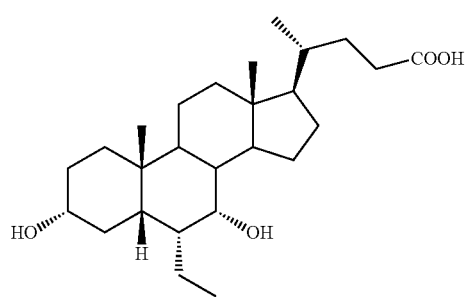

is an agonist of the farnesoid X receptor (FXR) and is in the pre-registration phase as active pharmaceutical ingredient for the treatment of various forms of hepatic cirrhosis, comprising non-alcoholic steatohepatitis. Obeticholic acid is known from EP 1 392 714, which describes its preparation starting from chenodeoxycholic acid of formula 2 according to the Scheme 1 reported below:

Scheme 1

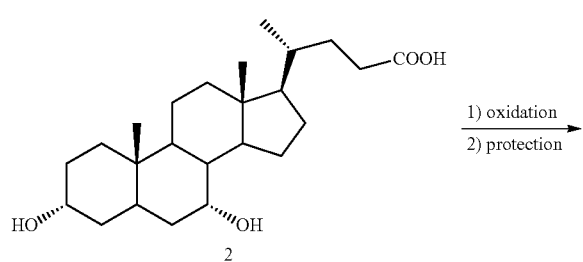

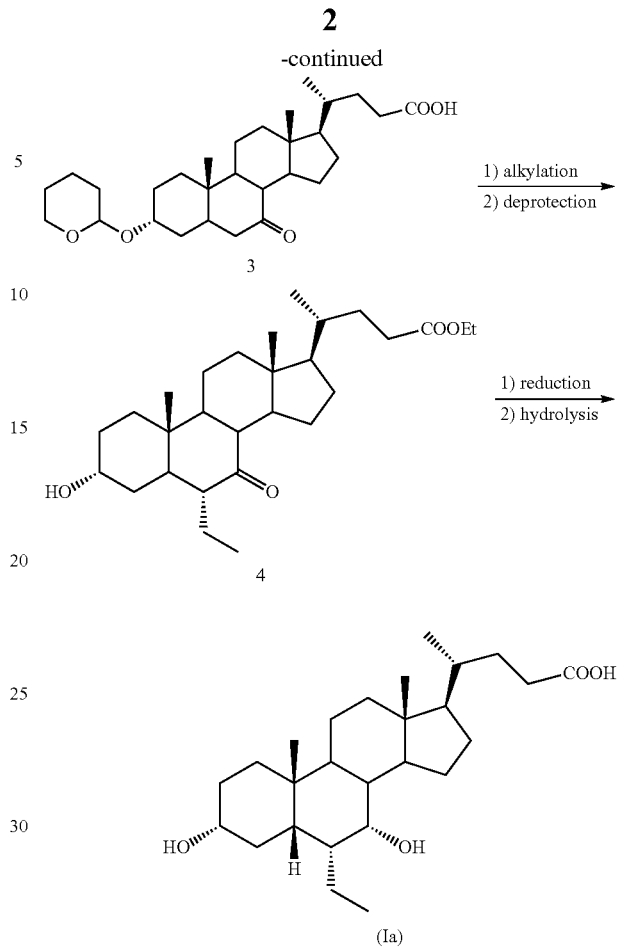

The synthesis for preparing obeticholic acid (Ia) starts from chenodeoxycholic acid of formula 2, which is an extensively used product by the pharmaceutical industry and which in turn is obtained from cholic acid, a major compound of the biliary acid mixture in bovine bile. The alkylation reaction of the anion of the protected ketone 3, prepared at −78° C. with BuLi, with EtBr to give the alkylated intermediate 4, represents the key step of the process. The yields of this step are low; the reaction conditions are not suitable for a process on an industrial scale and the synthesis is of limited efficiency. Subsequently, a new synthesis for preparing obeticholic acid was described in EP 1 888 614. The process as described in Scheme 2 consists in the conversion of compound 5 into the protected silyl ether 6. The preparation of the silyl ether is carried out by treating compound 5 with trimethylsilyl chloride at −78° C. using lithium diisopropylamide as base. Subsequently, the reaction of the silyl ether 6 and acetaldehyde in presence of $BF_3.Et_2O$ as Lewis acid provides the α,β-unsaturated ketone 7 in good yields. Hydrogenation of the double bond of 7 leads then to the ketone 8, which once reduced and hydrolyzed provides obeticholic acid of formula (Ia). This process, which starts as the previous one from chenodeoxycholic acid 2 and which is definitely more efficient than the previous one in respect to the yields, still suffers from the use of expensive bases prepared by using organolithium derivatives at low temperatures.

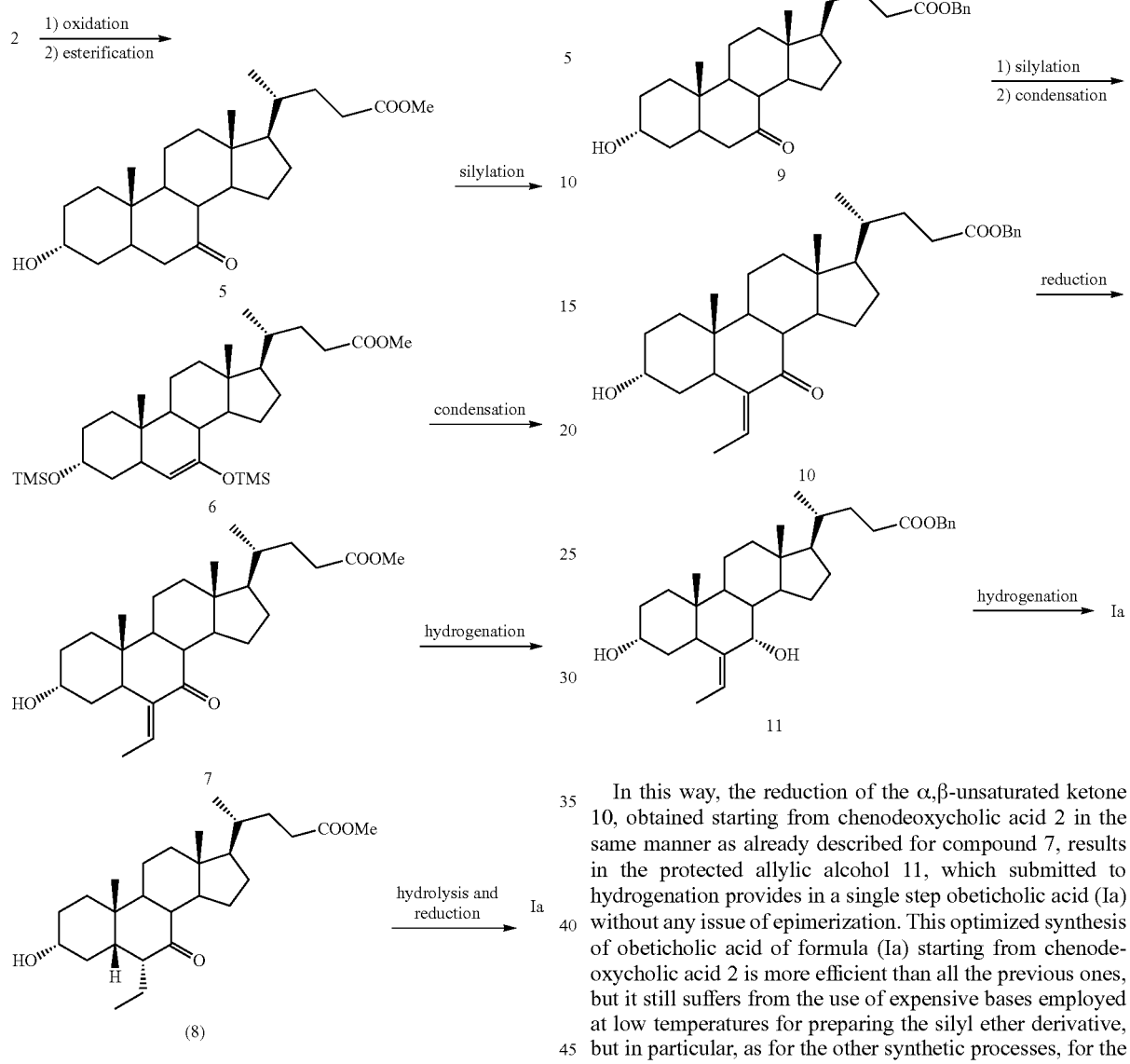

In addition, the authors of *J. Med. Chem* 2012, 55, 84-93 underlined different problems of epimerization of the carbon atom adjacent to the alkyl group of intermediate 8 during the reduction/alkaline hydrolysis of the methyl ester, while trying to repeat said process. For this reason, they suggested to substitute the methyl ester with the benzyl one and to revert the sequence of hydrogenation and reduction (Scheme 3).

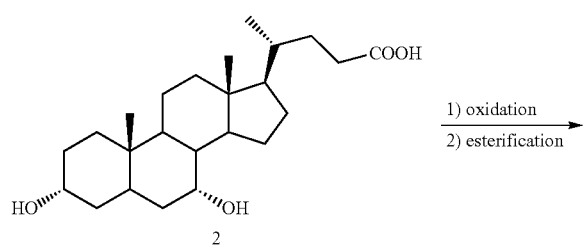

In this way, the reduction of the α,β-unsaturated ketone 10, obtained starting from chenodeoxycholic acid 2 in the same manner as already described for compound 7, results in the protected allylic alcohol 11, which submitted to hydrogenation provides in a single step obeticholic acid (Ia) without any issue of epimerization. This optimized synthesis of obeticholic acid of formula (Ia) starting from chenodeoxycholic acid 2 is more efficient than all the previous ones, but it still suffers from the use of expensive bases employed at low temperatures for preparing the silyl ether derivative, but in particular, as for the other synthetic processes, for the use of chenodeoxycholic acid 2 as starting material.

The above disclosed methods for preparing obeticholic acid of formula (Ia) have in common the problem to use the same starting material of animal or vegetable origin: chenodeoxycholic acid 2 is already used in the synthesis of further active pharmaceutical ingredients present on the market, and the availability of which, already difficult as such, may become much more difficult or even impossible in future.

In effect, chenodeoxycholic acid 2 is obtained industrially from cholic acid extracted from bovine bile. Its availability is limited by the number of the butchered bovines and because cholic acid is just a fraction of the bovine bile. Furthermore, it is already widely used for the preparation of ursodeoxycholic acid. Ursodeoxycholic acid is the most known first line drug for the treatment of primary biliary cirrhosis in the world.

CN 105777835, published on Jul. 20, 2016, that is after the priority date of Apr. 4, 2016 of the present application, discloses a further process for preparing obeticholic acid of formula (Ia) starting from 6-oxo-chenodeoxycholic acid alkyl ester 12. Wittig reaction with ethyltriphenylphosphonium salt in presence of a base provides the 6-ethylidene chenodeoxycholic acid alkyl ester 13, which once hydrogenated and deprotected gives obeticholic acid of formula (Ia) (Scheme 4):

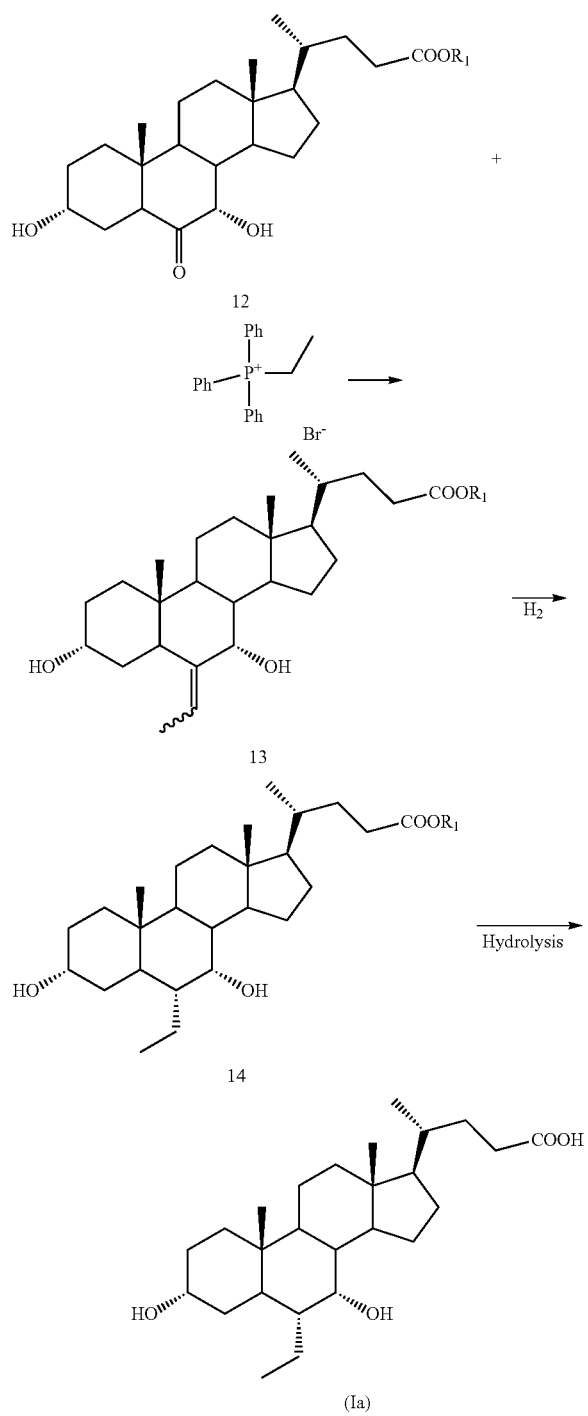

6-oxo-chenodeoxycholic acid methyl ester 12 can be prepared starting from hyodeoxycholic acid of formula (II) as described in *J. Chem. Soc. Perkin Trans* 1, 1990, pages 1-3.

The inventors of the present invention repeated several times the Wittig reaction of a compound of formula 12 with a phosphonium ylide as disclosed in CN 105777835, but they were not able to obtain the 6-ethylidene chenodeoxycholic acid alkyl ester of formula 13.

By considering in details the CN 105777835 procedure, it can be noted that the phosphonium ylide used in CN 105777835 is both a strong base and a nucleophile. Thus, in the specific process of CN 105777835, as confirmed by the experiments carried out by inventors of the present invention, the phosphonium ylide does not react with the carbonyl group, but likely just deprotonates the hydroxyls at positions C-3 and/or C-7.

Thus, it can be safely concluded that the procedures disclosed in CN 105777835 are not enabling.

Thus, there is still a need to have an efficient and economic process for the preparation of obeticholic acid of formula (Ia), which overcomes the drawbacks of the processes known in the art and which can be easily carried out on an industrial scale. Such process should not make use of natural starting materials used in the synthesis of other active ingredients, nor of reaction conditions or reagents, which are hardly compatible with synthetic processes on an industrial level.

SUMMARY OF THE INVENTION

The present invention is directed to the use of hyodeoxycholic acid of formula (II) for preparing obeticholic acid of formula (Ia). The process demonstrates to be particularly advantageous for an industrial application, since hyodeoxycholic acid of formula (II) is a waste product in the workup of swine bile.

DETAILED DESCRIPTION OF THE INVENTION

The inventors of the present invention have found a new and efficient method for preparing a compound of formula (I), in particular obeticholic acid of formula (Ia), as herein defined. This method is of particular advantage on an industrial scale, which as described below overcomes the synthetic drawbacks of the prior art and in particular makes use of a raw material of animal origin, hyodeoxycholic acid of formula (II), which today is considered only a waste product derived from the workup of swine bile. Thus, the new method for preparing obeticholic acid of formula (Ia) is not solely an alternative process for obtaining it, but, making use of a waste product, represents a considerable progress in the industrial field.

The invention provides as a first object a method for the preparation of a compound of formula (I), wherein the proton in H-5 can be in configuration 5α or 5β or a mixture thereof, preferably obeticholic acid of formula (Ia), wherein the proton in H-5 is in configuration 5β,

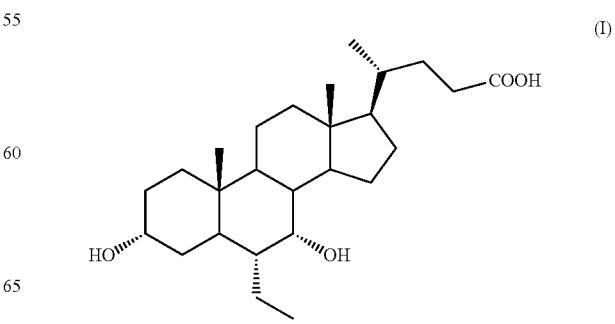

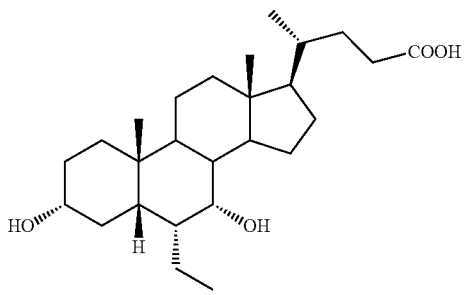

by a process comprising the use of 3α,6α-dihydroxy-5β-cholan-24-oic acid of formula (II), also known as hyodeoxycholic acid, as starting material,

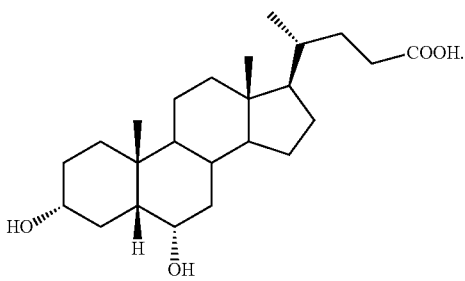

Hyodeoxycholic acid of formula (II) is a secondary biliary acid, which differs from the more famous chenodeoxycholic acid of formula 2, as defined above in Scheme 1, because it has the hydroxylic function in position C-6 instead of C-7 as in chenodeoxycholic acid of formula 2. Hyodeoxycholic acid is present in the bile of mammals in varying proportions, but it is the main constituent of the mixture of cholanic acids present in the swine bile, wherein it amounts almost to 40% of the total. In the past, it was used in the synthesis of progesterone. In the 50ies of the last century, the company Jenapharm of the former Eastern Germany used it as precursor for the synthesis of steroids. Recently, however, these syntheses have been abandoned and today hyodeoxycholic acid is only a waste product of the processing of porcine bile.

The authors of the present invention have surprisingly found that it is possible to obtain a compound of formula (I), in particular obeticholic acid of formula (Ia), from hyodeoxycholic acid of formula (II), which otherwise is a waste product, by a process which does not make use of low temperatures nor of expensive organometallic bases.

The problem of using hyodeoxycholic acid of formula (II) for preparing a compound of formula (I), in particular obeticholic acid of formula (Ia), is that the ethyl group has to be placed in position C-6 instead of the hydroxyl group and it is necessary to oxidize selectively position C-7 in such a way that a hydroxyl function is introduced in position α.

In the process of the invention, in the case it is necessary to protect the hydroxyl function in position C-3 and/or the carboxylic acid of a compound of the present invention and/or an intermediate thereof, before carrying out one of the aforementioned reactions, said chemical group can be protected and deprotected according to known methods. A thorough discussion for protection/deprotection steps is provided for example in Greene and Wuts (Greene, T. W.; Wuts, P. G. M. "Protective Groups in Organic Synthesis", John Wiley & Sons Inc., 1991) or in Kocienski (Kocienski, P. J. "Protecting Groups", George Thieme Verlag, 1994).

The hydroxyl group in position C-3 can be protected as ether, for instance as unsubstituted or substituted benzyl ether, for example as p-methoxy-benzyl ether, 3,4-dimethylbenzyl ether, benzhydryl ether; as tetrahydropyranyl ether or as silyl ether, for example as trimethylsilyl ether, triethylsilyl ether or tert-butyl-dimethylsilyl ether; or as ester, for example as formyl, acetyl, pivaloyl or benzoyl ester. Preferably, the hydroxyl group is protected as tetrahydropyranyl ether, trimethylsilyl ether or tert-butyl-dimethylsilyl ether, or as formyl, acetyl or pivaloyl ester.

Alternatively, the hydroxylic group in position C-3 can be selectively oxidized to a ketone with N-bromosuccinimide, and the ketone can be protected as acyclic or cyclic ketal, for example as dimethylketal, 1,3-dioxolane or 1,3-dioxanes. Once the protection in position C-3 is no longer necessary, the ketal can be deprotected to the ketone according to known methods and the obtained ketone can then be reduced to the hydroxyl group with a reducing agent, for instance with a hydride reducing agent, for example $NaBH_4$ or $LiAlH_4$.

The carboxylic acid group can be protected as ester, for instance as $C_1$-$C_6$ alkyl ester, wherein the $C_1$-$C_6$ alkyl group may be optionally substituted by phenyl. Preferably, the carboxylic acid group is protected as methyl, ethyl, isopropyl, tert-butyl or benzyl ester. The protection or deprotection of the carboxylic acid group can be carried out according to known methods. For instance, the ester can be prepared by activation of the carboxylate with a good leaving group as exemplified in Greene and Wuts mentioned above. Removal of the ester can be carried out according to known methods, for example cleavage of an ethyl or methyl ester with an acid or base or a benzyl ester by hydrogenation.

The authors of the present invention have found that a preferred process for preparing a compound of formula (I), in particular obeticholic acid of formula (Ia), starting from hyodeoxycholic acid of formula (II) is that in which first the ethyl group is placed in position C-6 instead of the hydroxyl and then the C-7 position is selectively oxidized.

The authors of the present invention have found an even more preferred process for preparing a compound of formula (I), in particular obeticholic acid of formula (Ia), starting from hyodeoxycholic acid of formula (II), by a method comprising the following steps:

I) oxidation of the hydroxyl group in position C-6 of hyodeoxycholic acid of formula (II) to the ketone;

II) reaction of the obtained ketone with an ethylidene phosphorane, preferably ethylidene triphenylphosphorane; and after said reaction with an ethylidene phosphorane, III) oxidation in position C-7 in such a way that a hydroxyl function is introduced in position α; or in alternative to step III)

IV) a) the allylic oxidation in position C-7 to a ketone and
b) subsequent reduction of the ketone in position C-7 to the α hydroxyl with a reducing agent, preferably with a hydride reducing agent, for example $NaBH_4$ or $LiAlH_4$, and wherein the hydroxyl group in position C-3 and the carboxylic acid group present in the compounds described in steps I)-IV) can be optionally protected.

Oxidation of the hydroxyl group in step I) can be carried out under conditions known in the art used for the conversion of a secondary alcohol to a ketone. For example, conditions and reagents can be those described below for step c).

The reaction of the ketone with an ethylidene phosphorane in step II) can be carried out under Wittig conditions. For example, conditions and reagents can be those described below for step d).

The oxidation in position C-7 in step III) can be carried out using an oxidizing agent in a solvent. For example, conditions and reagents can be those described below for step f).

The allylic oxidation in position C-7 to a ketone in step IV) a) can be carried out at conditions and with reagents as those described below for step j).

Reduction of the ketone to the α hydroxyl in step IV) b) can be carried out with a hydride reducing agent, for example $NaBH_4$ or $LiAlH_4$, in a solvent, for example an ether. Preferably, the reduction is carried out using $NaBH_4$ in a solvent, for example a dialkyl ether or tetrahydrofuran (THF).

A further object of the present invention is hyodeoxycholic acid of formula (II) for use in a process for preparing a compound of formula (I), in particular obeticholic acid of formula (Ia).

According to the process of the invention, a key compound in the preparation of a compound of formula (I), in particular of formula (Ia), is a compound of formula (VII)

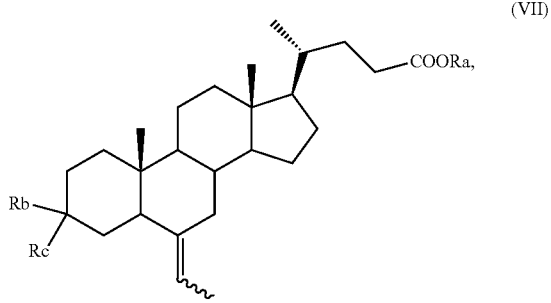

(VII)

wherein $R_a$ is hydrogen or an optionally substituted linear or branched $C_1$-$C_6$ alkyl group, or an optionally substituted aryl;

$R_b$ is hydrogen and $R_c$ is OH or O-PG, wherein PG is an alcohol protecting group as defined above, for instance an unsubstituted or substituted benzyl ether, a tetrahydropyranyl ether, a silyl ether, or an ester; or, alternatively, $R_b$ is $OR_1$ and $R_c$ is $OR_2$;

wherein each of $R_1$ and $R_2$, which may be the same or different, is a $C_1$-$C_6$ alkyl group, or $R_1$ and $R_2$ taken together form a —$(CH_2)_n$— chain, wherein n can be 2 or 3, and wherein the symbol ⌇ indicates that the absolute configuration of the double bond can be (E) or (Z) or a mixture thereof; and wherein the H-5 proton can be either in configuration 5α or 5β or a mixture thereof.

Preferably, the alcohol protecting group is tetrahydropyranyl ether, trimethylsilyl ether or tert-butyl-dimethylsilyl ether, or a formyl, acetyl or pivaloyl ester.

Preferably, a compound of formula (VII) is a compound of formula (VIIa), wherein the proton H-5 is in configuration 5β,

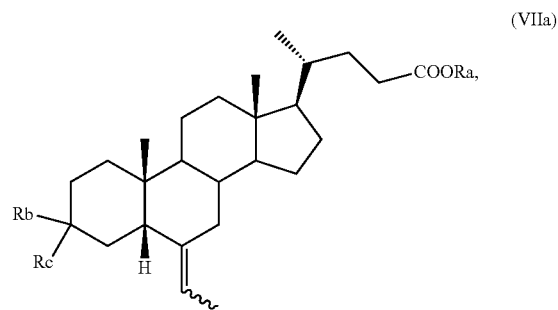

(VIIa)

and wherein $R_a$, $R_b$, $R_c$ and the symbol ⌇ are as defined above.

A $C_1$-$C_6$ alkyl group, which can be linear or branched, is typically a $C_1$-$C_4$ alkyl group, for instance methyl, ethyl, propyl, isopropyl, or butyl, isobutyl, tert-butyl, optionally substituted by one or more substituents, preferably from one to three substituents, which may be the same or different, such as halogen, for example chlorine or fluorine, or aryl, for example phenyl.

An aryl group may be, for example, a phenyl or naphthyl group, typically phenyl. Said aryl group may be optionally substituted by one to three substituents independently selected from a linear or branched $C_1$-$C_4$ alkyl group, which in turn may be optionally substituted by one to three halogen atoms, typically fluorine; a hydroxy group; a $C_1$-$C_4$ alkoxy group, for example methoxy; a halogen atom, such as bromine or chlorine; a cyano group; and a nitro group.

Preferably, the substituent $R_a$ in a compound of formula (VII) or (VIIa) is H, methyl or benzyl.

According to an aspect of the invention, a compound of formula (VII), as single isomer or as mixture of isomers, and in particular a compound of formula (VIIa), as defined above, and wherein $R_b$ is $OR_1$ and $R_c$ is $OR_2$ as defined above, can be obtained by a process comprising the following steps:

a) selective oxidation of the hydroxyl group in position C-3 of a compound of formula (III)

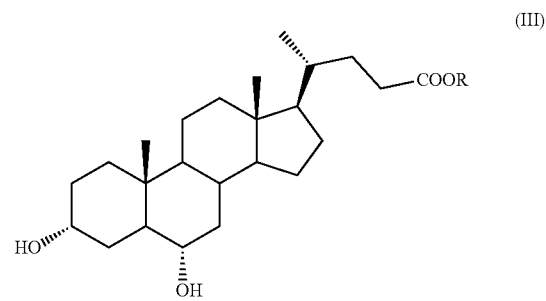

(III)

wherein R is an optionally substituted linear or branched $C_1$-$C_6$ alkyl group, or an optionally substituted aryl group, to obtain a compound of formula (IV):

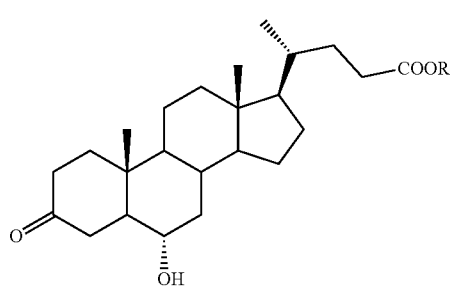

(IV)

wherein R is as defined above;

b) protection of the ketone group in C-3 position of a compound of formula (IV) to obtain a compound of formula (V):

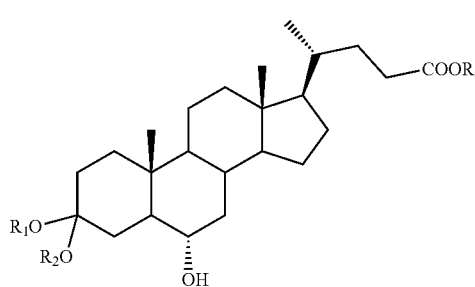

(V)

wherein $R_1$, $R_2$ and R are as defined above;

c) oxidation of the hydroxyl group in position C-6 of a compound of formula (V), and optional saponification of the ester group, to obtain a compound of formula (VI):

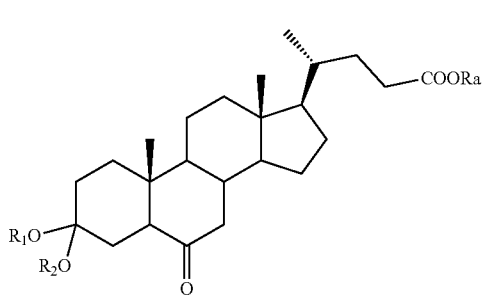

(VI)

wherein $R_a$, $R_1$ and $R_2$ are as defined above; and d) reaction of a compound of formula (VI) with a compound of formula (VIII):

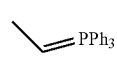

(VIII)

wherein Ph is phenyl, to obtain a compound of formula (VII); and in particular a compound of formula (VIIa).

A compound of formula (III) is a known compound, or can be obtained in an advantageous manner from hyodeoxycholic acid of formula (II) by e) protection of the carboxylic function of the hyodeoxycholic acid of formula (II) in order to obtain a compound of formula (III):

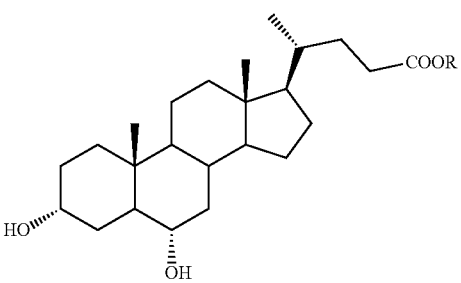

(III)

wherein R is as defined above.

In step a) of the synthesis, the protected ester of hyodeoxycholic acid of formula (III) is oxidized selectively at the C-3 position providing a compound of formula (IV). The selective oxidation at the C-3 required an optimization study. Indeed, the oxidation of the compound of formula (III) has been studied under different experimental conditions, for example under the Swern conditions, such as DMSO activated with $(COCl)_2$, using $KMnO_4$ or TEMPO as catalyst in presence of NaClO or $NaClO_2$, but in all cases only mixtures of products with mono or double oxidations of positions C-3 and C-6 were obtained. However, it was found that it is possible to obtain a compound of formula (IV) with high selectivity carrying out the oxidation with N-bromosuccinimide in a solvent. The oxidation reaction can be performed in a polar aprotic solvent selected, for example, in the group comprising dimethyl sulfoxide; acetonitrile; dimethylformamide or dimethylacetamide; a ketone, for example acetone or methylethylketone; water; or a mixture of two or more, preferably two or three, of said solvents.

According to a preferred aspect of the invention, the reaction can be carried out in presence of a mixture of water/acetone. Said reaction can be performed at a temperature comprised from about −10° C. to 50° C., preferably from about 0° C. to 10° C.

A preferred aspect of the invention is the oxidation of a compound of formula (III) with N-bromosuccinimide to obtain a compound of formula (IV).

According to step b), the ketone group at C-3 of a compound of formula (IV) is protected before oxidation at C-6.

The protection step can be performed according to known methods, for example in presence of a $C_1$-$C_4$ alcohol, of a diol, for example ethylene glycol or propylene glycol, or of vinyl ether and in presence of an acid catalyst, in order to provide a protected compound of formula (V), wherein $R_1$ and $R_2$ are as defined above. Preferably, the substituents $R_1$ and $R_2$ of a compound of formula (V) taken together form a —$(CH_2)_n$-chain, wherein n is 2.

According to step c), thanks to the protection of the ketone function at position C-3, the compound of formula (V) can be thus selectively oxidized at C-6, with following optional saponification of the ester group, to give a compound of formula (VI), wherein $R_a$, $R_1$ and $R_2$ are as defined above.

The oxidation reaction can be carried out under conditions known in the art used for the conversion of a secondary alcohol to a ketone. The reaction is preferably carried out at a pH value between about 4 and 10. These conditions permit to avoid the hydrolysis of the ester or acetal functionalities, which do occur at strongly basic or strongly acidic pH values. Preferably, the oxidation reaction is conducted in the presence of the catalyst TEMPO using NaClO or NaClO$_2$ as oxidizing agents in a solvent.

The solvent can be a polar aprotic solvent, such as dimethylformamide, dimethylsulfoxide or acetonitrile; an ethereal solvent, for example diethyl ether, methyl tert-butyl ether or tetrahydrofuran; a ketone, for example methyl ethyl ketone, methyl isobutyl ketone or acetone; an apolar aprotic solvent, for example hexane, heptane, toluene or xylene; an ester, for example an acetate of a linear or branched $C_1$-$C_5$ alcohol, preferably ethyl acetate; a chlorinated solvent, such as dichloromethane ($CH_2Cl_2$), chloroform or chlorobenzene; or water, or an aqueous solution of an inorganic salt able to generate a pH between about 7 and 10; or a mixture of two or more, typically two or three, of the above solvents. Preferably, the solvent is a biphasic system consisting of an organic solvent, preferably dichloromethane, and an aqueous solution at a pH between about 7 and 10.

The optional saponification of a compound of formula (VI) can be carried out according known methods.

According to step d), a compound of formula (VI) can be converted into a compound of formula (VII), preferably into a compound of formula (VIIa), as defined above, for example by a process carried out under Wittig conditions using a phosphorus ylide of formula (VIII), wherein Ph is phenyl, in a solvent.

(VIII)

The ylide of formula (VIII) can be simply prepared by treating an ethyltriphenylphosphonium salt with a strong base as well known to a person skilled in the art.

A strong base can be for example a strong organic base, for instance an alkaline metal alkoxide, preferably potassium tert-butylate or sodium tert-butylate; NaH; or lithium diisopropylamide (LDA).

The Wittig reaction can be performed at a temperature comprising between −10° C. and the reflux temperature of the solvent, preferably between about 0° C. and 30° C. During the conversion of a compound of formula (VI) into a compound of formula (VII) a partial epimerization of the C-5 of a compound formula (VI) can occur in the experimental conditions of the Wittig reaction. A compound of formula (VIIa), wherein the proton H-5 is in configuration 5β, can be isolated for example by crystallization, typically in a linear or branched $C_1$-$C_5$ alcohol, for instance methanol, ethanol isopropanol, n-butanol, iso-butanol or n-pentanol, preferably isopropanol.

In step e) of the synthesis, hyodeoxycholic acid of formula (II) is converted into a derivative with a protected carboxylic acid function, such as an ester of formula (III). Such protection can be carried out according to known methods in the art, for example in the field of steroid chemistry, by esterification of cholanic acids.

The inventors of the present invention have found that a compound of formula (VII), preferably of formula (VIIa), is a key compound for the preparation of a compound of formula (I), and preferably of obeticholic acid of formula (Ia).

A compound of formula (VII), in particular of formula (VIIa), which are new compounds, are further embodiments of the invention, as well as a compound of formula (VIIa) for use in a method for preparation of obeticholic acid of formula (Ia).

A further embodiment of the present invention is a compound of (VII) or of formula (VIIa) selected from:

3-spiro[1,3]dioxolane-(6E/Z)-ethyliden-5β-cholan-24-oic acid methyl ester;

3-spiro[1,3]dioxolane-6-ethyliden-cholan-24-oic acid;

3-spiro[1,3]dioxolane-(6Z)-ethylidene-5β-cholan-24-oic acid methyl ester; and

3α-(2,2-dimethylpropanoyl)-(6Z)-ethylidene-5β-cholan-24-oic acid methyl ester.

A compound of formula (VII), wherein $R_b$ is $OR_1$ and $R_c$ is $OR_2$ as defined above, can be converted into a compound of formula (I), as defined above, by a process further comprising:

f) stereoselective allylic oxidation of a compound of formula (VII) to obtain a compound of formula (IX):

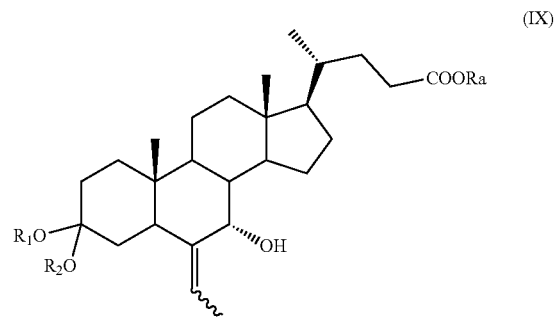

(IX)

wherein $R_a$, $R_1$ and $R_2$ and the symbol ⌇ are as defined above;

g) the removal of the protection at C-3 position of a compound of formula (IX) to obtain a compound of formula (X):

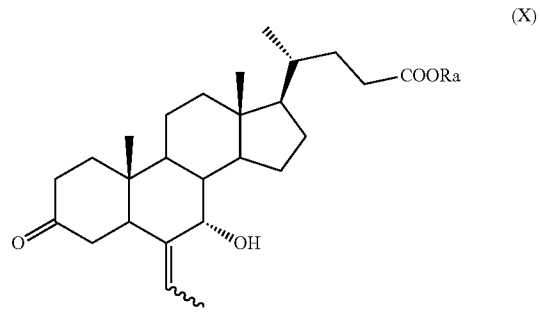

(X)

wherein the symbol ⌇ and $R_a$ are as defined above;

h) the stereoselective reduction of the ketone group at C-3 position of a compound of formula (X) to obtain a compound of formula (XI):

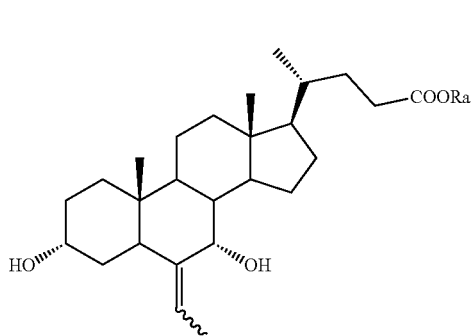

(XI)

wherein the symbol ⌇ and $R_a$ are as defined above; and i) the hydrogenation of a compound of formula (XI) to obtain a compound of formula (I); or j) allylic oxidation in position C-7 of a compound of formula (VII) to obtain a compound of formula (XII):

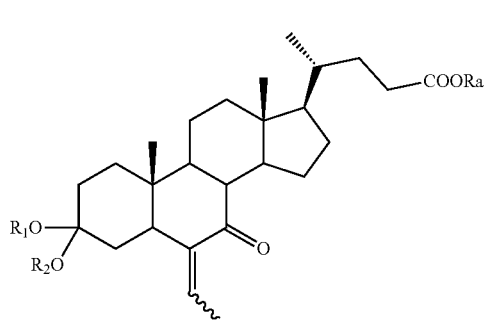

(XII)

wherein the symbol ⌇, $R_a$, $R_1$ and $R_2$ are as defined above;

k) the removal of the protection at C-3 position of a compound of formula (XII) to obtain a compound of formula (XIII):

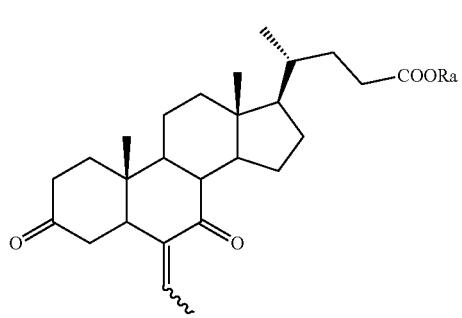

(XIII)

wherein the symbol ⌇ and $R_a$ are as defined above and optional saponification;

l) the hydrogenation of a compound of formula (XIII) to obtain a compound of formula (XIV):

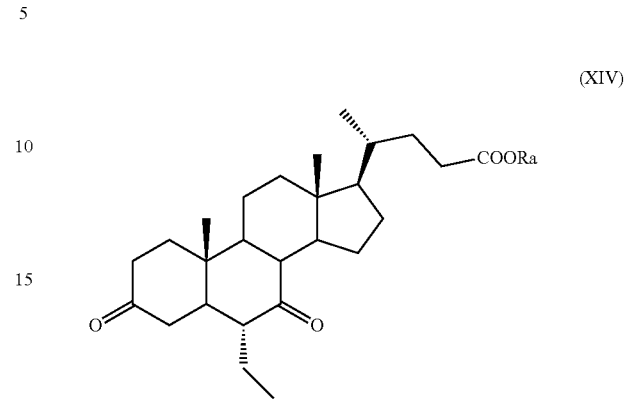

(XIV)

wherein $R_a$ is as defined above; and m) reduction of a compound of formula (XIV) to obtain a compound of formula (I).

In particular, a compound of formula (VII), and preferably a compound of (VIIa), can be converted into a compound of formula (I), and preferably into a compound of formula (Ia), as defined above, by a process further comprising:

n) the removal of the protection at C-3 position of a compound of formula (VII), or (VIIa), to obtain a compound of formula (XV), or (XVa), respectively,

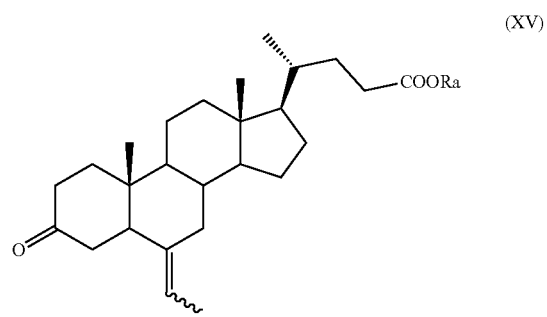

(XV)

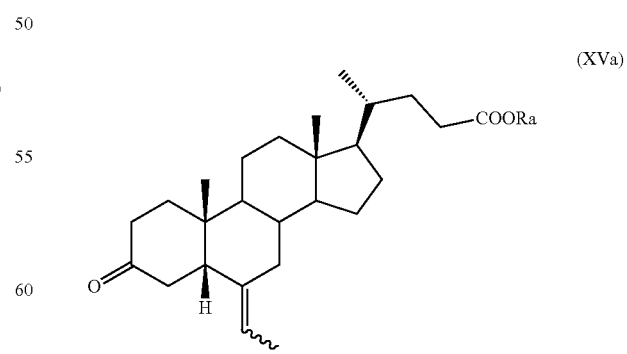

(XVa)

wherein the symbol ⌇ and $R_a$ are as defined above;

o) the stereoselective reduction of the ketone group at the C-3 position of a compound of formula (XV), or (XVa), to obtain a compound of formula (XVI), or (XVIa), respectively, and optional saponification of the ester function:

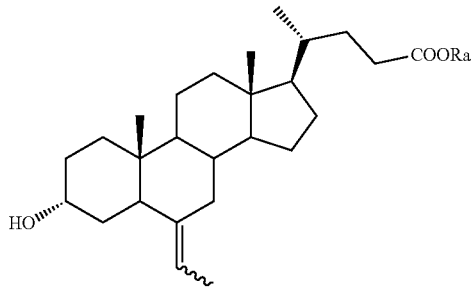
(XVI)

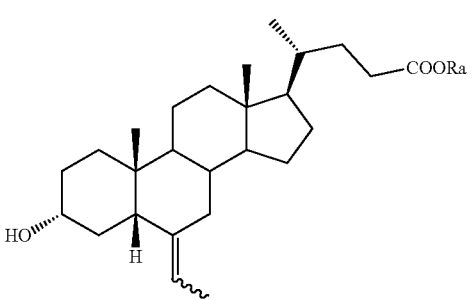
(XVIa)

wherein the symbol ⌇ and $R_a$ are as defined above; and
p) the allylic oxidation in position C-7 in a compound of formula (XVI) or (XVIa), and optional saponification of the ester function, to obtain a compound of formula (XI) or (XIa), respectively:

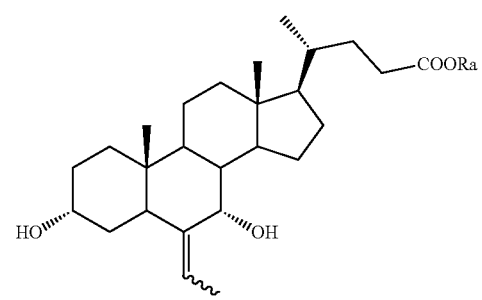
(XI)

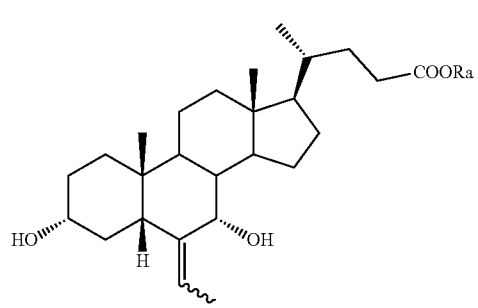
(XIa)

wherein the symbol ⌇ and $R_a$ are as defined above;
q) the hydrogenation of a compound of formula (XI), or (XIa), to obtain a compound of formula (I), as defined above, or obeticholic acid of formula (Ia); or r) the protection of the hydroxyl group at C-3 position and allylic oxidation of position C-7 of a compound of formula (XVI), or (XVIa), or the allylic oxidation of position C-7 of a compound of formula (VII), or (VIIa), and optional saponification of the ester function, to obtain a compound of formula (XVII), or (XVIIa)

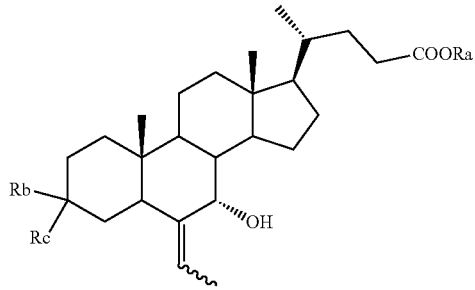
(XVII)

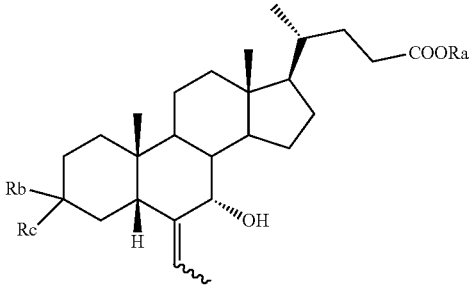
(XVIIa)

wherein the symbol ⌇ and $R_a$, $R_b$ and $R_c$ are as defined above;
s) the oxidation of the hydroxyl group in position C-7 to the keto group and the removal of the protection at C-3 of a compound of formula (XVII) or (XVIIa) to obtain a compound of formula (XVIII) or (XVIIIa):

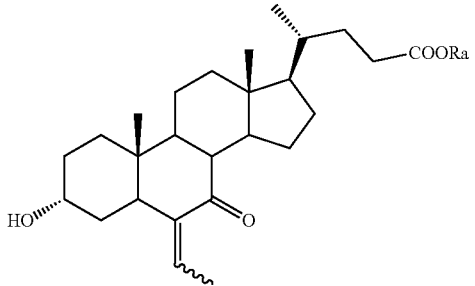
(XVIII)

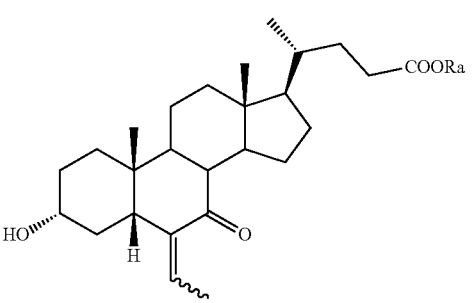
(XVIIIa)

wherein the symbol ⌇ and $R_a$ are as defined above;

t) the hydrogenation and reduction of a compound of formula (XVIII) or (XVIIIa) to obtain a compound of formula (I) or (Ia).

In a preferred aspect of the invention a compound of formula (VIIa) is a key compound in the process for preparation obeticholic acid of formula (Ia), which can be preferably obtained according to the synthetic sequence from n) to q) or r) to t).

The stereoselective allylic oxidation of a compound of formula (VII) according to step f), or of a compound of formula (XVI) or (XVIa) according to step p) or of a compound of formula (VII), (VIIa), (XVII), or (XVIIa) according to step r) can be carried out using an oxidizing agent in a solvent.

An oxidizing agent can be for example $SeO_2$, $MnO_2$ or a peroxyester, for example tert-butyl perbenzoic acid, in presence of a Cu(I) salt or of Pd, Ru or Rh complexes, or a hydroperoxide, for example tert-butyl hydroperoxide, catalyzed by Cu/Al oxides.

The allylic oxidation can be performed at a temperature comprised from about −10° C. to the reflux temperature of the solvent, preferably between about 20° C. and 80° C.

The solvent may be a polar aprotic solvent, such as dimethylformamide, dimethylsulfoxide or acetonitrile; an ethereal solvent, for example methyl tert-butyl ether, tetrahydrofuran or dioxane; a ketone, e.g. methyl ethyl ketone, methyl isobutyl ketone or acetone; an apolar aprotic solvent, for example hexane, heptane, toluene or xylene; an ester, for example an acetate of a linear or branched $C_1$-$C_5$ alcohol, preferably ethyl acetate; a chlorinated solvent, such as dichloromethane ($CH_2Cl_2$), chloroform or chlorobenzene; or water; or a mixture of two or more, typically two or three, of the above solvents.

According to step g), k) or n), the acetal protection of a compound of formula (IX), of formula (XII), of formula (VII) or of formula (VIIa) can be removed providing a compound of formula (X), of formula (XIII), of formula (XV) or of formula (XVa), respectively, wherein $R_a$ is as defined above.

The reaction can be performed in an acidic aqueous solution, according to methods known to the skilled person, used for the hydrolysis of acetals The compounds of formula (IX), (X), (XII), (XIII), (XV), (XVa), (XVI), (XVIa), (XVII), or of formula (XVIIa) are new and are a further embodiment of the present invention.

A further embodiment of the present invention is a compound of formula (IX), (X), (XII), (XIII), (XV), (XVa), (XVI), (XVIa), (XVII), or of formula (XVIIa), in particular a compound selected from:
3-spiro[1,3]dioxolane-6-ethyliden-7α-hydroxy-5β-cholan-24-oic acid methyl ester;
3-oxo-6-ethylidene-5β-cholan-24-oic acid methyl ester;
3α-hydroxy-(6Z)-ethylidene-5β-cholan-24-oic acid methyl ester;
3α-(2,2-dimethylpropanoyl)-7α-hydroxy-(6E)-ethylidene-5β-cholan-24-oic acid methyl ester.

Another embodiment of the present invention is the use of a compound of formula (IX), (X), (XII), (XIII), (XV), (XVI) or (XVII) for the preparation of a compound of formula (I) and the same compounds for the use in a method for the preparation of a compound of formula (I).

A further embodiment of the present invention is the use of a compound of formula (XVa), (XVIa) or (XVIIa) for the preparation of obeticholic acid of formula (Ia), and the same compound for the use in a method for the preparation of obeticholic acid of formula (Ia).

The stereoselective reduction of the ketone group at C-3 in a compound of formula (X), of formula (XV) or of formula (XVa) according to steps h) or o), or of a compound of formula (XVIII) or (XVIIIa) according to steps t) can be carried out with a hydride reducing agent, for example $NaBH_4$ or $LiAlH_4$, in a solvent, for example an ether. According to step m), a compound of formula (XIV) can be reduced by a reducing step analogous to the ones reported in *Chemistry Letters*, 1996, 5, 335-336, or in *Steroids*, 2006, 71(6), 469-475, with a hydride reducing agent, for example $NaBH_4$ or $LiAlH_4$, in a solvent, for example an ether, as indicated above.

Preferably, the reduction in steps h), m) or o) can be carried out using $NaBH_4$ in tetrahydrofuran (THF).

The hydrogenation of a compound of formula (XI), or of formula (XIa) to obtain a compound of formula (I), in particular of obeticholic acid of formula (Ia), according to the steps i) and q), or of formula (XIII) according to the step l), or of a compound of formula (XVIII) or (XVIIIa) according to steps t) can be carried out according to known methods, in particular as described in *J. Med. Chem* 2012, 55, 84-93, in a mixture of THF/methanol using Pd/C as catalyst. Optionally, a crude product of formula (XIa) as obtained after the hydrogenation can be purified by crystallization in order to obtain pure obeticholic acid of formula (Ia). For example, hydrogenation in step l) of a compound of formula (XIII) to obtain a compound of formula (XIV), as defined above, can be performed as reported in EP 1 888 614.

The hydrogenation of a compound of formula (XI), (XIa) or (XIII) can be carried out by catalytic hydrogenation in presence of homogenous or heterogeneous metal catalyst, for example a Pd, Pt, Ni, Rh or Ru catalyst, preferably a Pd catalyst.

In case of an heterogeneous metal catalyst, the catalyst is preferably placed on an inert support, such as, for example, carbon, barium hydroxide, alumina, calcium carbonate; preferably charcoal. The concentration of the metal on the support may vary between about 1% and 30%, preferably between about 5% and 20%.

The employed hydrogen pressure may vary from about 1 atm to 40 atm, preferably from about 1 atm to 10 atm.

The molar quantity of the used catalyst, referred to a compound of formula (XIII), is comprised between about 0.1 and 10%, preferably between about 0.5 and 5%.

The reaction can be carried out in presence of an organic solvent selected, for example, from a polar aprotic solvent, such as dimethylformamide, dimethylacetamide acetonitrile or dimethylsulfoxide; an acyclic or cyclic ethereal solvent, typically tetrahydrofuran or methyl tert-butyl ether; a chlorinated solvent, typically dichloromethane; an apolar aprotic solvent, for example toluene or hexane; a polar protic solvent, for example a linear or branched $C_1$-$C_6$ alcohol, in particular methanol, ethanol, isopropanol or butanol; an ester, for example ethyl acetate, isopropyl acetate or butyl acetate; a linear or branched $C_3$-$C_7$ ketone, for example acetone, methyl ethyl ketone, methyl isobutyl ketone; a carboxylic acid, for example acetic acid or propionic acid; or water; or a mixture of two or more, typically two or three, of the above solvents.

Alternatively, the hydrogenation reactions can be carried out in a solution of a mineral acid or base, for example hydrochloric acid or sulfuric acid, or sodium or potassium hydroxide; or a mixture of them with one, two or three organic solvents indicated above.

Said hydrogenation reactions can be performed at a temperature comprised from about 0° C. and the reflux temperature of the solvent, preferably between about 25° C. and the reflux temperature.

The hydrogenation reaction of a compound of formula (XI), (XIa) or (XIII) can be carried out by a hydrogen transfer reaction, using a homogeneous or heterogeneous metal catalyst, for example those defined above, and a hydrogen donor. The latter can be selected for example from the group comprising cyclohexene; cyclohexadiene; methylcyclohexene; limonene; dipentene; menthene; hydrazine; phosphinic acid or its derivatives, such as sodium hypophosphite; indoline; ascorbic acid; formic acid or its sodium or ammonium salts; and secondary alcohols, for example isopropanol. A preferred hydrogen donor is ammonium formate.

The molar ratio between the hydrogen donor and the compound of formula (XIII) can be between about 1.5 and 50, preferably between about 1.5 and 10.

The reduction by the hydrogen transfer reaction can be carried out in presence of an organic solvent, selected for example from one of the above mentioned solvents.

The allylic oxidation in position C-7 in a compound of formula (VII) according to step j) to obtain a compound of formula (XII), as defined above, can be performed in the conditions as described for an allylic oxidation described previously, which results immediately from the alkene to the enone instead of the allylic alcohol, as described for example in Synthesis 2013, 45, 2201-2221. Preferably, the oxidation can be carried out using metal oxidizing systems based on Cr, Cu, Se, Rh, Co, Ru, Pd and in absence of a metallic oxidant in the presence of NaClO, NaClO$_2$, NaIO$_4$, O$_2$ or an organic peroxide, for example tert-butylhydroperoxide.

The protection of the hydroxyl group at C-3 position in step r) and the removal of the protecting group in step s) can be performed according to known methods. For example, the hydroxyl group can be protected as ester by reaction with an acyl chloride or anhydride in presence of a base, for example pyridine or trimethylamine (TEA). The cleavage of the ester can be performed for example by treatment with a base, for example sodium hydroxide. Alternatively, the hydroxyl group can be protected as ether by reaction with dihydropyran, unsubstituted or substituted benzyl halide or a silyl halide, wherein the halide can be chloride or bromide. The cleavage of the tetrahydropyran or the silyl ether can be performed for example by treatment with an acid, and the benzyl protecting group by hydrogenation.

The oxidation of the hydroxyl in position C-7 to its keto derivative of step s) can be performed according to known methods. For example, the hydroxyl group can oxidized with IBX or an IBX adduct, for instance as described in Mendeleev Comm. 2012, 22, 129-131 or in PCT/EP2016/070883.

A further embodiment of the present invention is directed to a pharmaceutical composition comprising a compound of formula (Ia), thus being 6α-ethyl-3α,7α-dihydroxy-5β-cholan-24-oic acid, also known as 6α-ethyl-chenodeoxycholic acid, obeticholic acid or as 6-ECDCA,

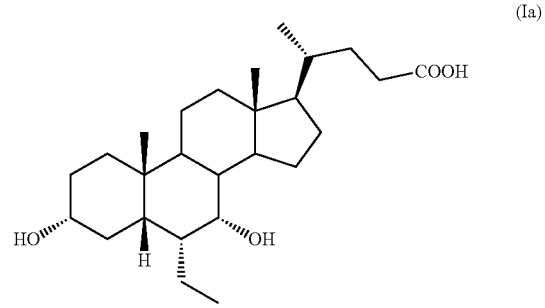 [SMILES: CC[C@H]1[C@@H](O)C2C3CC[C@H]([C@H](C)CCC(=O)O)[C@@]3(C)CCC2[C@@]2(C)CC[C@@H](O)C[C@@H]12]

(Ia)

and a pharmaceutically acceptable carrier, wherein the obeticholic acid of formula (Ia) does not comprise chenodeoxycholic acid of formula 2. The pharmaceutical composition can be prepared according to known methods.

Chenodeoxycholic acid of formula 2 and obeticholic acid of formula (Ia) have similar physicochemical properties and as asserted by Dr. Melissa Rewolinski under C.F.R. § 1.132 during the prosecution of U.S. Pat. No. 9,238,673 signed on Sep. 25, 2015, a separation by chromatography, even by HPLC, would be impractical.

The process of preparing obeticholic acid of formula (Ia) according to the present invention is consequently of particular advantage, since it does not make use of chenodeoxycholic acid of formula 2. Accordingly, obeticholic acid of formula (Ia), as obtained by the process of the present invention, is free from chenodeoxycholic acid 2. Therefore, there is no need to separate said products.

The following examples further illustrate the invention.

Example 1: Synthesis of
3α-oxo-6α-hydroxy-5β-cholan-24-oic acid methyl
ester of Formula (IV) with R=Me Hyodeoxycholic acid methyl ester (16.0 g, 39.4 mmol) of formula (III) is dissolved in a solution of 160 mL of acetone and 80 mL of water in a 250 mL three-neck flask comprising a thermometer and a magnetic stirrer. The obtained solution is cooled down to a temperature between 0 and 5° C. and N-bromosuccinimide (11.9 g, 67.0 mmol) is added portionwise as solid. The reaction mixture is stirred at a temperature between 0 and 5° C. for 3 hours, then treated with 5% NaOH solution (70 mL) and stirred for an additional hour. The mixture is then concentrated under reduced pressure and extracted with toluene. The obtained organic layer is first washed with a 5% NaOH solution, then with a saturated solution of NaCl. The obtained organic phase is used as such in the subsequent reaction. An aliquot of the solution is concentrated to dryness and analyzed.

$^1$H-NMR (CDCl$_3$, 400 MHz, 24° C.) δ: 0.65 (3H, s); 0.89 (3H, d, J=6.4 Hz); 0.97 (3H, s); 2.36-1.07 (27H, m); 3.62 (3H, s); 4.04 (1H, m).

$^{13}$C-NMR (CDCl$_3$, 100 MHz, 24° C.) δ: 213.20, 174.71, 67.36, 56.08, 55.89, 51.49, 50.21, 42.80, 40.19, 39.80, 37.10, 37.05, 36.13, 36.10, 35.28, 34.50, 34.19, 30.99, 30.90, 28.07, 24.15, 22.82, 21.07, 18.24, 12.03.

Example 2: Synthesis of 3-spiro[1,3]dioxolane-6α-
hydroxy-5β-cholan-24-oic acid methyl ester of Formula (V) with R=Me; R$_1$ and R$_2$ Taken Together
Form a —(CH$_2$)$_n$— Chain, Wherein n is 2

The solution as obtained in Example 1 is treated with ethylene glycol (10.9 g, 175 mmol) and paratoluenesulfonic acid (0.0750 g, 0.395 mmol) in a 250 mL three-neck flask comprising a thermometer, a magnetic stirrer and a Dean-Stark apparatus. The solution is heated to reflux to remove the water/toluene azeotrope and stirred for 2 hours. At the end of the reaction the mixture is cooled down to about 20° C. and stirred for at least a further hour to allow the product to precipitate. The mixture is filtered off and the solid washed with water and pre-cooled diethyl ether. Then, the solid is dried under reduced pressure to obtain the 3-spiro[1,3]dioxolane-6α-hydroxy-5β-cholan-24-oic acid methyl ester of formula (V) (14.9 g, 33.2 mmol) with a yield of 85%, calculated from the hyodeoxycholic acid methyl ester of formula (III). The product is analyzed by $^1$H and $^{13}$C-NMR and results to be sufficiently pure to be used in the next step without any further purification.

$^1$H-NMR (CDCl$_3$, 400 MHz, 24° C.) δ: 0.63 (3H, s); 0.90 (3H, d, J=6.4 Hz); 0.92 (3H, s); 1.04-2.49 (26H, m); 3.70 (3H, s); 3.94 (4H, m); 4.05 (1H, m).

$^{13}$C-NMR (CDCl$_3$, 100 MHz, 24° C.) δ: 174.79, 109.71, 67.83, 64.20, 64.09, 56.13, 55.86, 51.49, 47.26, 42.82, 39.91, 39.15, 35.88, 35.31, 34.63, 34.58, 34.38, 31.02, 30.93, 30.13, 28.68, 28.09, 24.15, 23.25, 20.97, 18.23, 12.02.

Example 3: Synthesis of the 3-spiro[1,3]dioxolane-6-oxo-5β-cholan-24-oic acid methyl ester of Formula (VI) with R$_a$=Me; R$_1$ and R$_2$ Taken Together Form a —(CH$_2$)$_n$— Chain, Wherein n is 2

3-Spiro[1,3]dioxolane-6α-hydroxy-5β-cholan-24-oic acid methyl ester of formula (V), as prepared in Example 2 (14.9 g, 33.2 mmol), KBr (1.97 g, 16.6 mmol), Bu$_4$NBr (0.640 g, 1.99 mmol), Na$_2$HPO$_4$.2H$_2$O (0.71 g, 4.0 mmol) and NaH$_2$PO$_4$.H$_2$O (0.79 g, 0.57 mmol) are dissolved in a mixture composed by CH$_2$Cl$_2$ (150 mL) and water (40 mL) in a 500 mL three-neck flask comprising a mechanical stirrer, thermometer and a dropping funnel. The obtained biphasic mixture is cooled down to 0° C. and treated with TEMPO (0.16 mg, 0.99 mmol) and a 1.9% solution of NaOCl (143.0 mL, 36.49 mmol) keeping the temperature below 5° C. Once the addition is completed, the reaction mixture is stirred for 30 minutes and then treated with MeOH. After 15 minutes the organic phase is then separated and washed with a solution of 5% HCl (2×50 mL), a solution of 5% NaOH (2×50 mL) and with a saturated NaCl solution (50 mL) and finally dried over anhydrous Na$_2$SO$_4$. After filtration, the solution is concentrated under reduced pressure providing the 3-spiro[1,3]dioxolane-6-oxo-5β-cholan-24-oic acid methyl ester of formula (VI) (14.5 g, 32.4 mmol) with a yield of 97%.

The product was analyzed by $^1$H and $^{13}$C-NMR and resulted to be sufficiently pure to be used in the next step without any further purification.

$^1$H-NMR (CDCl$_3$, 200 MHz, 24° C.) δ: 0.71 (3H, s); 0.91 (3H, s); 0.97 (3H, d, J=6.2 Hz); 1.04-2.49 (26H, m); 3.71 (3H, s); 3.97 (4H, m).

$^{13}$C-NMR (CDCl$_3$, 50 MHz, 24° C.) δ: 213.60, 174.77, 108.23, 64.68 (2C), 58.73, 57.17, 56.12, 51.82, 43.44, 43.09, 39.97, 39.67, 38.23, 37.26, 35.62, 34.76, 33.69, 31.38, 31.27, 30.55, 28.35, 24.30, 23.34, 21.49, 18.61, 12.36.

Example 4: Synthesis of the 3-spiro[1,3]dioxolane-(6E/Z)-ethyliden-5β-cholan-24-oic acid methyl ester of Formula (VII) with R$_a$=Me; R$_1$ and R$_2$ Taken Together Form a —(CH$_2$)$_n$— Chain, Wherein n is 2

Ethyltriphenylphosphonium bromide (10.80 g, 29.14 mmol) is suspended under inert atmosphere in 70 mL of anhydrous THF in a 250 mL three-neck flask comprising a dropping funnel, a thermometer and a magnetic stirrer. The mixture is cooled down to 0° C., solid t-BuOK (3.20 g, 28.6 mmol) is added portionwise and the mixture is stirred for 40 minutes. Then, a solution of 3-spiro[1,3]dioxolane-6-oxo-5β-cholan-24-oic acid methyl ester of formula (VI) (5 g, 11.2 mmol), prepared as described in Example 3, in 30 mL of THF is added. The reaction mixture is stirred for 18 hours and the temperature was raised within the same time to room temperature. At the end of the reaction the mixture is treated with water (1.0 g, 55 mmol) and concentrated under reduced pressure. The obtained residue is purified by silica gel chromatography (toluene/acetone 90/10), providing the 3-spiro[1,3]dioxolane-(6E/Z)-ethyliden-5β-cholan-24-oic acid methyl ester of formula (VII) (2.82 g, 6.16 mmol) as solid amorphous diastereoisomeric mixture (E)/(Z).

$^1$H-NMR (CDCl$_3$, 200 MHz, 24° C.) δ: (diagnostic signals, mixture E/Z) 0.61-0.63 (9H, m); 0.80 (3H, m), 0.90 (6H, d, J=6.4 Hz); 1.59-1.53 (6H, m); 3.64 (6H, s); 3.92 (8H, m); 4.87 (1H, q, J=6.8 Hz), 5.18 (1H, q, J=6.6 Hz).

$^{13}$C-NMR (CDCl$_3$, 50 MHz, 24° C.) δ: (mixture E/Z) 174.14, 139.13, 117.00, 112.99, 109.53, 109.00, 63.87, 63.79, 56.12, 55.52, 54.42, 51.13, 48.36, 43.14, 42.49, 39.94, 39.62, 37.42, 36.80, 36.53, 35.43, 35.35, 35.03, 34.76, 33.90, 33.52, 33.11, 30.68, 29.76, 27.83, 23.88, 22.41, 21.22, 20.83, 17.97, 12.55, 12.13, 11.83, 11.78, 11.40.

Example 5: Synthesis of 3-spiro[1,3]dioxolane-6-oxo-cholan-24-oic acid of Formula (VI) with R$_a$=H; R$_1$ and R$_2$ Taken Together Form a —(CH$_2$)$_n$— Chain, Wherein n is 2

3-spiro[1,3]dioxolane-6-oxo-5β-cholan-24-oic acid methyl ester of formula (VI) (11.0 g, 24.6 mmol), as prepared as in Example 3, is dissolved in 22 mL of MeOH in a 100 mL three-neck flask comprising a dropping funnel, a thermometer and a magnetic stirrer. The mixture is cooled down to 0° C. and treated with a solution of 30% of NaOH (11 mL). The reaction mixture is stirred for 18 hours at room temperature, then cooled down to 0° C. and treated with HCl 37% until reaching a pH of 2. The methanol is evaporated under reduced pressure, the aqueous phase is extracted with CH$_2$Cl$_2$ and the organic phase dried over anhydrous Na$_2$SO$_4$ and concentrated to residue. 3-Spiro[1,3]dioxolane-6-oxo-cholan-24-oic acid of formula (VI) (10.9 g, 24.0 mmol) is obtained in a quantitative yield.

$^1$H-NMR (CDCl$_3$, 200 MHz, 24° C.) δ: 0.65 (3H, s); 0.74 (3H, s); 0.91 (3H, d, J=6.2 Hz); 1.04-2.57 (26H, m); 3.97 (4H, m).

$^{13}$C-NMR (CDCl$_3$, 50 MHz, 24° C.) δ: 211.71, 180.11, 109.36, 64.56, 64.48, 57.02, 56.33, 56.05, 53.84, 46.93, 43.37, 41.22, 39.82, 38.19, 36.03, 35.58, 31.35, 31.22, 31.04, 30.14, 28.26, 24.29, 21.80, 18.57, 12.84, 12.40.

Example 6: Synthesis of 3-spiro[1,3]dioxolane-6-ethyliden-cholan-24-oic acid of Formula (VII) with R$_a$=H; R$_1$ and R$_2$ Taken Together Form a —(CH$_2$)$_n$— Chain, Wherein n is 2

Ethyltriphenylphosphonium bromide (42.70 g, 115.1 mmol) is suspended under inert atmosphere in anhydrous THF (340 mL) in a 250 mL three-neck flask comprising a dropping funnel, a thermometer and a mechanical stirrer. The mixture is cooled down to 0° C. and t-BuOK (12.64 g, 113.9 mmol) is added portionwise as solid and stirred for 40 minutes, then treated with a solution of 3-spiro[1,3]dioxolane-6-oxo-cholan-24-oic acid of formula (VI) (10.9 g, 25.3 mmol), prepared as described in Example 5, in 85 mL of THF. The reaction mixture is stirred for 18 hours at room temperature, then treated with acetic acid (8.30 g, 139 mmol). After 30 minutes of further stirring, the mixture is filtered and the obtained solution concentrated under reduced pressure. The residue is then purified by crystallization from a solution of methanol:water 2:1. After filtration and drying 3-spiro[1,3]dioxolane-6-ethyliden-cholan-24-oic acid of formula (VII) (7.50 g, 16.9 mmol) is obtained with a yield of 67%.

$^1$H-NMR (CDCl$_3$, 200 Mhz, 24° C.) δ: (diagnostic signals) 0.64 (6H, s); 0.92 (3H, d, J=6.4 Hz); 1.59 (3H, d, J=6.8 Hz); 3.93 (4H, s); 4.89 (1H, q, J=6.8 Hz).

$^{13}$C-NMR (CDCl$_3$, 50 Mhz, 24° C.) δ: 180.49, 139.80, 113.69, 110.32, 64.50, 64.42, 56.77, 56.16, 55.07, 49.03, 43.18, 40.28, 38.09, 37.19, 35.99, 35.66, 34.55, 33.73, 31.40, 31.25, 31.12, 28.45, 24.53, 21.86, 18.59, 13.17, 12.50, 12.04.

Example 7: Synthesis of 3-spiro[1,3]dioxolane-6-ethyliden-7α-hydroxy-5β-cholan-24-oic acid methyl ester of Formula (IX) with R=Me; $R_1$ and $R_2$ Taken Together Form a —(CH$_2$)$_n$— Chain, Wherein n is 2

3-Spiro[1,3]dioxolane-6-ethyliden-5β-cholan-24-oic acid methyl ester of formula (VII) (2.50 g, 5.46 mmol), as prepared as in Example 4, is dissolved in 15 mL of dioxane in a 50 mL two-neck flask comprising a thermometer and a magnetic stirrer and the obtained solution is treated with SeO$_2$ (1.51 g, 13.6 mmol). The reaction mixture is stirred for 20 hours, then diluted with 5 mL of a solution of HCl at 5% and stirred for a further hour, then filtered on celite. The solution is concentrated under reduced pressure and diluted with 20 mL of CH$_2$Cl$_2$. The organic phase is washed with a saturated solution of NaCl and concentrated under reduced pressure. Then, the residue is purified by silica gel chromatography (CH$_2$Cl$_2$: acetone 95:5), providing 3-spiro[1,3]dioxolane-6-ethyliden-7α-hydroxy-5β-cholan-24-oic acid methyl ester of formula (IX) (1.20 g, 2.53 mmol) diastereoisomeric mixture (E)/(Z) as amorphous solid with a yield of 47%.

$^1$H-NMR (CDCl$_3$, 200 MHz, 24° C.) δ: (diagnostic signals of the mixture E/Z) 0.62 (3H, s); 0.63 (3H, s); 0.64 (3H, s); 0.77 (3H, s); 0.91 (6H, d, 6.2 Hz); 1.61 (3H, d, J=6.8 Hz); 1.65 (3H, dd, J1=7.0 Hz, J2=1.4 Hz); 3.65 (6H, s); 3.92 (8H, m); 4.55 (2H, d, J=2.0 Hz); 5.05 (1H, q, J=6.8 Hz); 5.50 (1H, q, J=6.6 Hz).

$^{13}$C-NMR (CDCl$_3$, 50 MHz, 24° C.) δ: (mixture E/Z) 174.91, 142.30 (E), 141.58 (Z), 123.97 (E), 117.29 (Z), 110.11 (Z), 109.39, 64.55, 64.46, 56.02, 51.78, 50.58, 50.45, 46.31, 43.11, 42.61, 40.83, 40.37, 39.80, 35.71, 33.62, 31.34, 28.45, 23.92, 22.77, 21.65, 18.60, 12.74, 12.18, 12.05, 10.97.

$^1$H-NMR (CDCl$_3$, 200 MHz, 24° C.) δ: (diagnostic signals of isomer Z) 0.63 (3H, s); 0.77 (3H, s); 0.91 (3H, d, 6.2 Hz); 1.65 (3H, dd, J1=7.0 Hz, J2=1.4 Hz); 3.65 (3H, s); 3.92 (4H, m); 4.55 (1H, d, J=2.0 Hz); 5.05 (1H, q, J=6.8 Hz).

$^{13}$C-NMR (CDCl$_3$, 50 MHz, 24° C.) δ: (isomer Z) 174.89, 141.63, 117.16, 110.10 (C-3), 66.29 (C-7), 64.52 (2C), 56.02, 51.77, 50.56, 46.27, 43.09, 42.58, 40.83, 39.77, 38.02, 35.71 (2C), 33.61, 31.33 (3C), 28.44, 23.90, 21.65, 18.58, 12.94, 12.18, 10.96.

Example 8: Synthesis of 3α,7α-dihydroxy-6-ethyliden-5β-cholan-24-oic acid methyl ester of Formula (XI) with $R_a$=Me 3-Spiro[1,3]dioxolane-6-ethyliden-7α-hydroxy-5β-cholan-24-oic acid methyl ester of formula (IX) (1.10 g, 2.32 mmol), obtained as described in Example 7, and p-toluenesulfonic acid (110 mg, 0.580 mmol) are dissolved in 25 mL of a mixture of 99:1 acetone:water in a 100 mL two-neck flask comprising a thermometer, a reflux condenser and a magnetic stirrer. The reaction mixture is stirred for 9 hours at about 25° C., then treated with 5 mL of an aqueous solution of NaHCO$_3$ at 5% and concentrated to residue.

The raw mixture is extracted with CH$_2$Cl$_2$ (10 mL) and the organic phase washed with a saturated solution of NaCl (2×5 mL), dried over Na$_2$SO$_4$ and filtered. 3-Oxo-6-ethyliden-7α-hydroxy-5β-cholan-24-oic acid methyl ester (X) in configuration (Z) (900 mg) is obtained after evaporation of the solvent under reduced pressure. NaBH$_4$ (53.0 mg, 1.39 mmol) is suspended under inert atmosphere in 2 mL of a mixture of THF:MeOH 9:1 at 0° C. in a 10 mL two-neck flask comprising a thermometer and a reflux condenser and the 3-oxo-6-ethyliden-7α-hydroxy-5β-cholan-24-oic acid methyl ester of formula (X) (400 mg) is added once the formation of hydrogen is terminated. The reaction mixture is stirred for further 3 hours, then treated with 1 mL of a solution of HCl at 10% and diluted with 10 mL of CH$_2$Cl$_2$. The organic phase is washed with a saturated solution of NaCl (5 mL), dried over anhydrous Na$_2$SO$_4$, filtered and concentrated under reduced pressure. The obtained residue is purified by silica gel chromatography (toluene:acetone 90:10) providing 130 mg (0.30 mmol) of 3α,7α-dihydroxy-6-ethyliden-5β-cholan-24-oic acid methyl ester of formula (XI) with a yield of 30%.

$^1$H-NMR (CDCl$_3$, 200 MHz, 24° C.) δ: (diagnostic signals) 0.61 (3H, s); 0.64 (3H, s); 0.90 (3H, d, J=6.0 Hz); 1.65 (3H, dd, J1=7.0 Hz, J2=1.4 Hz); 3.61 (1H, m); 3.64 (3H, s); 4.55 (1H, d, J=2.0 Hz); 5.05 (1H, q, J=6.8 Hz).

$^{13}$C-NMR (CDCl$_3$, 50 MHz, 24° C.) δ: 174.98, 141.48, 117.53, 71.96 (C-3), 66.40 (C-7), 56.09, 51.82, 50.63, 46.66, 43.51, 43.15, 40.87, 39.79, 38.09, 36.82, 35.74, 33.86, 31.54, 31.37 (2C), 28.47, 23.92, 21.73, 18.60, 12.97, 12.20, 11.82.

Example 9: Synthesis of 3α,7α-dihydroxy-6-ethyliden-5β-cholan-24-oic acid of Formula (XI) with $R_a$=H 3α,7α-Dihydroxy-6-ethyliden-5β-cholan-24-oic acid methyl ester of formula (XI), with $R_a$=Me as obtained in Example 8, (80 mg, 0.19 mmol) is dissolved in 3 mL of a mixture of MeOH:NaOH at 30% 2:1 in a 10 mL one-neck flask. The mixture is stirred for 18 hours, then acidified with aqueous HCl until reaching pH=1 and extracted several times with CH$_2$Cl$_2$. The obtained organic phase is dried over anhydrous Na$_2$SO$_4$, filtered and concentrated under reduced pressure. 3α,7α-Dihydroxy-6-ethyliden-5β-cholan-24-oic acid of formula (XI), wherein $R_a$ is H, (75 mg, 0.18 mmol) is obtained as a white crystalline solid with a yield of 96%.

$^1$H-NMR (CDCl$_3$, 200 MHz, 24° C.) δ: (diagnostic signals) 0.65 (3H, s); 0.69 (3H, s); 0.95 (3H, d, J=6.2 Hz); 1.67 (3H, dd, J1=6.8 Hz, J2=1.4 Hz); 3.58 (1H, m); 4.55 (1H, d, J=0.6 Hz); 5.05 (1H, q, J=6.8 Hz).

$^{13}$C-NMR (CD$_3$OD, 50 MHz, 24° C.) δ: 176.92, 142.15, 116.07, 71.33, 65.58, 56.27, 50.44, 46.57, 43.30, 42.82, 41.01, 39.86, 37.79, 36.79, 35.70, 33.25, 31.30, 30.97, 30.90, 28.16, 23.49, 21.53, 17.84, 11.67, 11.34, 11.02.

Example 10: Synthesis of 3-spiro[1,3]dioxolan-(6Z)-ethylidene-5β-cholan-24-oic acid methyl ester of Formula (VIIa)

Ethyltriphenylphosphonium bromide (98.0 g, 0.264 mol) is suspended in THF (650 mL) under inert atmosphere is a one liter three-neck reactor equipped with a reflux condenser, thermometer and a mechanical stirrer. The mixture is cooled down to 0° C. and treated with solid t-BuOK (29.0 g, 0.258 mol) added portionwise. The suspension is stirred for 60 minutes, then treated with a solution of 3-spiro[1,3]dioxolane-6-oxo-5β-cholan-24-oic acid methyl ester of formula (VI) (25 g, 0.056 mol), obtained as described in Example 3, in 150 mL of THF. At the end of the reaction the mixture is diluted with water (120 mL) and the organic phase is separated and concentrated under reduced pressure. The residue is extracted with heptane (2×100 mL), the combined organic phases are washed with water (100 mL) and concentrated under reduced pressure. The so obtained raw material is crystallized from isopropanol. After filtration and drying 3-spiro[1,3]dioxolan-(6Z)-ethylidene-5β-cholan-24-oic acid methyl ester of formula (VIIa) (4.6 g, 0.010 mol) is obtained with a yield of 18%.

$^1$H-NMR (300 MHz, CDCl$_3$) δ: 5.20 (1H, q, J=6.6 Hz), 3.98-3.88 (4H, m), 3.66 (3H, s), 2.62-2.54 (1H, m), 1.04-2.4 (26H, m), 1.56 (3H, d, J=6.9 Hz), 0.91 (3H, d, J=6.0 Hz), 0.81 (3H, s), 0.62 (3H, s).

Example 11: Synthesis of 3-oxo-6-ethylidene-5β-cholan-24-oic acid methyl ester of Formula (XVa)

3-Spiro[1,3]dioxolan-6-ethylidene-5β-cholan-24-oic acid methyl ester of formula (VIIa), obtained as described in Example 10, (1.30 g, 2.83 mmol) is suspended under nitrogen in a mixture of acetone (15 mL) and HCl 5% (5 mL) in a 50 mL three-neck flask comprising a thermometer, a reflux condenser. The reaction mixture is stirred with a magnetic stirrer at room temperature for 6 hours, then the acetone is distilled off and the residual suspension is diluted with H$_2$O (10 mL). The obtained solid is filtered, washed with H$_2$O (3×10 mL) and dried under vacuum at 50° C. for 4 hours. 1.18 g of 3-oxo-(6Z)-ethylidene-5β-cholan-24-oic acid methyl ester of formula (XVa) are obtained in quantitative yields.

$^1$H-NMR (300 MHz, CDCl$_3$) δ: 5.25 (1H, q, J=6.6 Hz), 3.66 (3H, s), 2.78-1.04 (26H, m), 1.53 (3H, d, J=6.6 Hz), 0.92 (3H, d, J=6.3 Hz), 0.88 (3H, s), 0.66 (3H, s).

Example 12: Synthesis of 3α-hydroxy-(6Z)-ethylidene-5β-cholan-24-oic acid methyl ester of Formula (XVIa)

3-Oxo-6-ethylidene-5β-cholan-24-oic acid methyl ester of formula (XVa), obtained as described in Example 11, (1.18 g, 2.85 mmol) is dissolved at room temperature and under nitrogen in a mixture of methanol (6 mL) and THF (6 mL) in a 50 mL three-neck flask equipped with a thermometer and a reflux condenser. The obtained solution is cooled down to 0° C., and NaBH$_4$ (0.108 g, 2.85 mmol) is added portion wise as solid. The solution is stirred at 0° C. for 30 minutes, then poured into a solution of 1 M HCl (10 mL) at 0° C. The obtained mixture is stirred for 15 minutes and then extracted with CH$_2$Cl$_2$ (2×10 mL). The combined organic phases are concentrated under reduced pressure and the obtained residue is purified by silica gel chromatography (toluene:acetone=95:5) providing 900 of 3α-hydroxy-(6Z)-ethylidene-5β-cholan-24-oic acid methyl ester of formula (XVIa) with a yield of 76%.

$^1$H-NMR (300 MHz, CDCl$_3$) δ: 5.20 (1H, q, J=6.9 Hz), 3.54-3.72 (4H, m), 2.40-1.00 (26H, m), 1.54 (3H, d, J=6.6 Hz), 0.91 (3H, d, J=6.3 Hz), 0.78 (3H, s), 0.63 (3H, s).

Example 13: Synthesis of 3α,7α-dihydroxy-(6E)-ethylidene-5β-cholan-24-oic acid methyl ester of Formula (XIa)

3α-Hydroxy-6-ethylidene-5β-cholan-24-oic acid methyl ester of formula (XVIa), obtained in Example 12, (0.9 g, 2.17 mmol) is dissolved in dioxane (15 mL) at room temperature and under nitrogen atmosphere in a 50 mL three-neck flask equipped with a thermometer and a reflux condenser. Water (60 µl) and SeO$_2$ (289 mg, 2.60 mmol) are added and the reaction mixture is heated to 60° C. After stirring for 1 hour, the solution is concentrated under reduced pressure. Then, the residue is portioned between CH$_2$Cl$_2$ (10 mL) and H$_2$O (10 mL), the phases are separated and the organic phase concentrated under reduced pressure. The so obtained raw material is purified by silica gel chromatography (CH$_2$Cl$_2$:acetone=80:20), giving 500 mg of 3α,7α-dihydroxy-(6E)-ethylidene-5β-cholan-24-oic acid methyl ester of formula (XIa) with a yield of 50%.

$^1$H-NMR (300 MHz, CDCl$_3$) δ: 5.49 (1H, q, J=6.9 Hz), 3.96-3.86 (1H, m), 3.65 (3H, s), 3.56-3.44 (1H, m), 2.40-1.00 (24H, m), 1.59 (3H, d, J=6.9 Hz), 0.91 (3H, d, J=6.0 Hz), 0.73 (3H, s), 0.62 (3H, s).

Example 14: Synthesis of 3α,7α-dihydroxy-(6E)-ethylidene-5β-cholan-24-oic Acid of Formula (XIa)

3α,7α-Dihydroxy-(6E)-ethylidene-5β-cholan-24-oic acid methyl ester of formula (XIa), obtained in Example 13, (500 mg, 1.16 mmol) is dissolved at room temperature and under nitrogen in methanol (5 mL) in a 50 mL three-neck flask equipped with a thermometer and a reflux condenser. NaOH 30% (687 mg, 5.15 mmol) is added and the reaction is carried out under stirring for 16 hours at room temperature. The solution is then acidified with HCl 37% to pH 1, diluted with water (10 mL) and extracted with CH$_2$Cl$_2$ (2×5 mL). The combined organic phases are concentrated under reduced pressure and the obtained residue is purified by silica gel chromatography (CH$_2$Cl$_2$:MeOH=90:10) giving 300 mg of 3α,7α-dihydroxy-(6E)-ethylidene-5β-cholan-24-oic acid of formula (XIa) with a yield of 62%.

$^1$H-NMR (300 MHz, CDCl$_3$) δ: 5.49 (1H, q, J=6.9 Hz), 3.92-3.96 (1H, m), 3.46-3.56 (1H, m), 2.40-1.00 (24H, m), 1.59 (3H, d, 6.6 J=Hz), 0.92 (3H, d, 6.0 J=Hz), 0.73 (3H, s), 0.63 (3H, s).

Example 15: Synthesis of 3α-(2,2-dimethylpropanoyl)-(6Z)-ethylidene-5β-cholan-24-oic acid methyl ester of Formula (VIIa)

3.38 g (8.11 mmol) of 3α-hydroxy-(6Z)-ethylidene-5β-cholan-24-oic acid methyl ester of formula (XVIa), as obtained in Example 12, are dissolved in THF (20 ml) at room temperature and under nitrogen atmosphere in a 50 mL three-neck flask equipped with a thermometer and a reflux condenser. TEA (3.4 ml; 24.3 mmol) and pivaloyl chloride (2 ml, 16.2 mmol) are added and the reaction mixture is heated to reflux. After stirring for 16 hours, the solution is concentrated under reduced pressure. Then, the residue is diluted with EtOAc (30 ml) and washed with HCl 5% (20 ml), NaHCO$_3$ saturated solution (20 ml) and H$_2$O (20 ml). The organic phase is concentrated under reduced pressure giving 3.17 g of 3α-(2,2-dimethylpropanoyl)-(6Z)-ethylidene-5β-cholan-24-oic acid methyl ester of formula (VIIa) with a yield of 78%.

¹H-NMR (300 MHz, CDCl₃) δ: 5.20 (1H, q, J=6.9 Hz), 4.80-4.66 (1H, m), 3.66 (3H, s), 2.40-1.00 (38H, m), 0.91 (3H, d, J=6.3 Hz), 0.79 (3H, s), 0.63 (3H, s).

Example 16: Synthesis of 3α-(2,2-dimethylpropanoyl)-7α-hydroxy-(6E)-ethylidene-5β-cholan-24-oic acid methyl ester of Formula (XVIIa)

0.5 g (1 mmol) of the 3α-(2,2-dimethylpropanoyl)-(6Z)-ethylidene-5β-cholan-24-oic acid methyl ester of formula (VIIa), as obtained in Example 15, are dissolved in dioxane (7.5 ml) at room temperature and under nitrogen atmosphere in a 50 mL three-neck flask equipped with a thermometer and a reflux condenser. Water (20 μl) and SeO₂ (133 mg, 1.2 mmol) are added and the reaction mixture is heated to 60° C. and stirred for 2 hour, then concentrated under reduced pressure. The so obtained raw material is purified by silica gel chromatography (toluene:acetone=97.5:2.5), giving 100 mg of 3α-(2,2-dimethylpropanoyl)-7α-hydroxy-(6E)-ethylidene-5β-cholan-24-oic acid methyl ester of formula (XVIIa) with a yield of 20%.

¹H-NMR (300 MHz, CDCl₃) δ: 5.49 (1H, q, J=6.9 Hz), 4.66-4.54 (1H, m), 3.94 (1H, s), 3.64 (3H, s), 2.40-1.00 (37H, m), 0.91 (3H, d, J=6.30 Hz), 0.75 (3H, s), 0.63 (3H, s).

Example 17: Synthesis of 3α-hydroxy-7-oxo-(6E)-ethylidene-5β-cholan-24-oic Acid of Formula (XVIIIa) and its Conversion into Obeticholic Acid of Formula (Ia)

0.1 g (0.19 mmol) of 3α-(2,2-dimethylpropanoyl)-7α-hydroxy-(6E)-ethylidene-5β-cholan-24-oic acid methyl ester of formula (XVIIa), as obtained in Example 16, is dissolved in THF (1 ml) at room temperature and under nitrogen atmosphere in a 20 mL two-neck flask. 2-Iodoxybenzoic acid (IBX) adduct with quinoline (80 mg, 0.20 mmol), prepared as disclosed in PCT/EP2016/070883, are added and the reaction mixture is heated to 50° C. and stirred for 2 hour, then filtered and concentrated under reduced pressure. Then, the residue is diluted with CH₂Cl₂ (2 ml) and washed with HCl 5% (2 ml), NaHCO₃ saturated solution (2 ml) and H₂O (2 ml). The organic phase is concentrated under reduced pressure giving 105 mg of raw material that is dissolved in methanol (2 ml) and treated with NaOH 30% (0.5 ml). The solution is stirred for 48 hours, then acidified with HCl 37% until reaching pH 1 and concentrated under reduced pressure. The obtained residue is purified by silica gel chromatography (CH₂Cl₂:acetone=95:5) giving 43 mg of 3α-hydroxy-7-oxo-(6E)-ethylidene-5β-cholan-24-oic acid of formula (XVIIIa) with a yield of 5β%.

¹H-NMR (300 MHz, CDCl₃) δ: 6.18 (1H, q, J=6.9 Hz), 3.70-3.58 (1H, m), 2.60-1.10 (29H, m), 1.00 (3H, s), 0.94 (3H, d, J=6.3 Hz), 0.64 (3H, s).

3α-Hydroxy-7-oxo-(6E)-ethylidene-5β-cholan-24-oic acid of formula (XVIIIa) can be converted into obeticholic acid of formula (Ia) according to known methods. For example, 3α-hydroxy-7-oxo-(6E)-ethylidene-5β-cholan-24-oic acid of formula (XVIIIa) can be hydrogenated with Pd/C and hydrogen gas, e.g. according to the teaching of EP 1 888 614 or U.S. Pat. No. 9,238,673, and reduced with NaBH₄ as described in Example 12 of the present invention.

Alternatively, the 3α-hydroxy-7-oxo-(6E)-ethylidene-5β-cholan-24-oic acid of formula (XVIIIa) can be converted into its C₁-C₆ alkyl ester according to the methods disclosed above, and then converted into obeticholic acid of formula (Ia) by hydrogenation of the (6E)-ethylidene group, reduction of the 7-oxo group and deprotection of the ester according to known methods.

The invention claimed is:

1. A process for the preparation of a compound of formula (Ia):

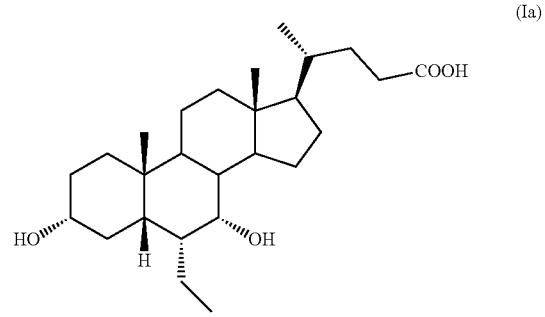 [SMILES: CC[C@H]1[C@@H](O)C2C3CC[C@H]([C@H](C)CCC(=O)O)[C@@]3(C)CCC2[C@@]2(C)CC[C@@H](O)C[C@@H]12]

wherein the proton H-5 of the compound of formula (Ia) is in configuration 5β, wherein hyodeoxycholic acid having the following formula (II)

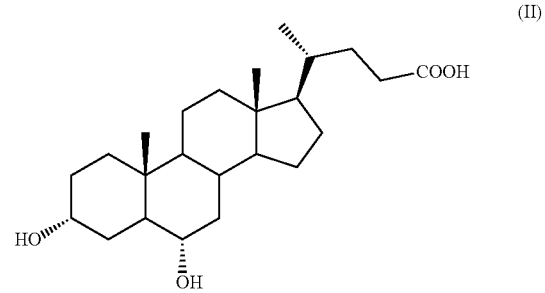 [SMILES: C[C@H](CCC(=O)O)[C@H]1CCC2C3C[C@H](O)C4C[C@H](O)CC[C@]4(C)C3CC[C@@]21C]

is used as the starting material, comprising
   a) introducing an ethyl group in position C-6;
   b) oxidizing position C-7 to introduce a hydroxyl function in position α; or
   allylic oxidation in position C-7 to a ketone and subsequently reducing the ketone in position C-7 to an α hydroxyl with a reducing agent.

2. The process according to claim 1, wherein first the ethyl group is placed in position C-6 and then the C-7 position is selectively oxidized.

3. The process according to claim 1, wherein the hydroxyl group in position C-3 and the carboxylic acid group are optionally protected.

4. The process according to claim 3, wherein step a) comprises:
   I) oxidizing the hydroxyl group in position C-6 of hyodeoxycholic acid of formula (II) to the ketone;
   II) reacting the obtained ketone with an ethylidene phosphorane
   III)
   IV).

5. The process according to claim 4, comprising the preparation of a compound of formula (VII)

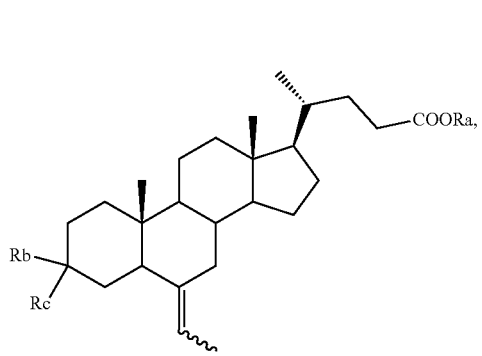
(VII)

wherein R<sub>a</sub> is hydrogen or an optionally substituted linear or branched C₁-C₆ alkyl group, or an optionally substituted aryl;

R$_b$ is hydrogen and R$_c$ is OH or O-PG, wherein PG is an alcohol protecting group; or R$_b$ is OR$_1$ and R$_c$ is OR$_2$;

wherein each of R$_1$ and R$_2$, which are the same or different, is a C$_1$-C$_6$ alkyl group, or R$_1$ and R$_2$ taken together form a —(CH$_2$)$_n$— chain, wherein n is 2 or 3, wherein the symbol ⌇ indicates that the absolute configuration of the double bond can be (E) or (Z) or a mixture thereof; and wherein the H-5 proton is either in configuration 5α or 5β, or a mixture thereof, comprising the reaction of a compound of formula (VI)

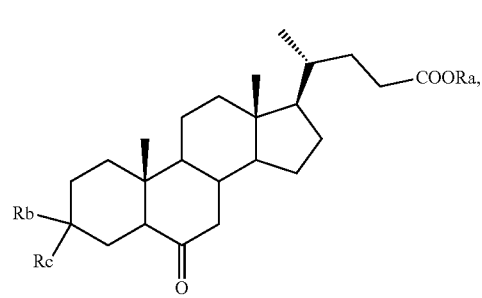
(VI)

wherein R$_a$, R$_b$ and R$_c$ are as defined above, with a compound of formula (VIII)

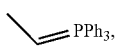
(VIII)

wherein Ph is phenyl.

6. The process according to claim 5, wherein the compound of formula (VII) is a compound of formula (VIIa):

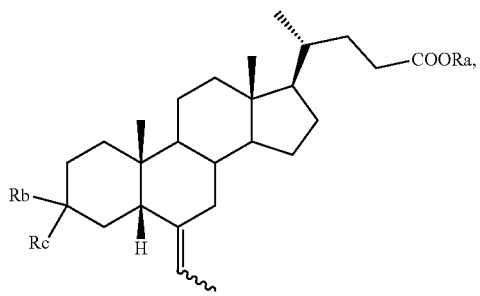
(VIIa)

wherein the symbol ⌇, R$_a$, R$_b$ and R$_c$ are as defined in claim 5 and the proton H-5 of the compound of formula (VIIa) is in configuration 5β;

comprising reacting a compound of formula (VI):

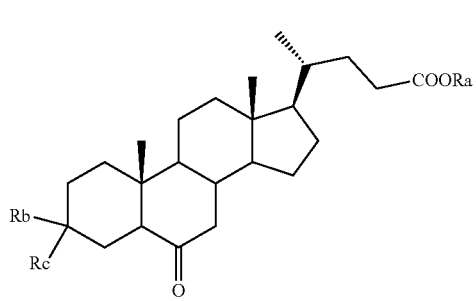
(VI)

with a compound of formula (VI):

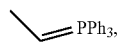
(VIII)

wherein Ph is phenyl;

and separating a compound of formula (VIIa) having the proton H-5 in configuration 5β, by crystallization.

7. The process according to claim 5, wherein R$_b$ is OR$_1$ and R$_c$ is OR$_2$, and R$_1$ and R$_2$ are as defined in claim 5, wherein a compound of formula (VI) is prepared by a process comprising the following steps:

a) selective oxidation of the hydroxyl group in C-3 position of a compound of formula (III)

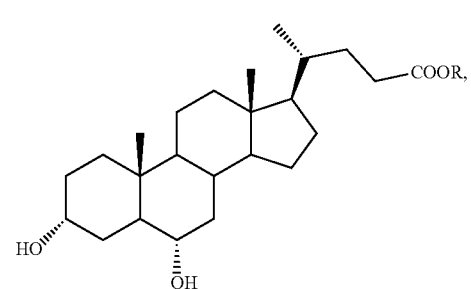
(III)

wherein R is an, optionally substituted, linear or branched C₁-C₆ alkyl group, or an optionally substituted aryl group, to obtain a compound of formula (IV):

(IV)

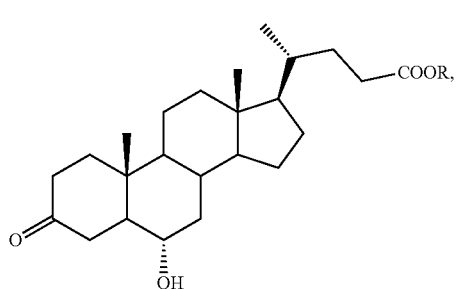

wherein R is as defined above;

b) protection of the ketone group in C-3 position of a compound of formula (IV) to obtain a compound of formula (V):

(V)

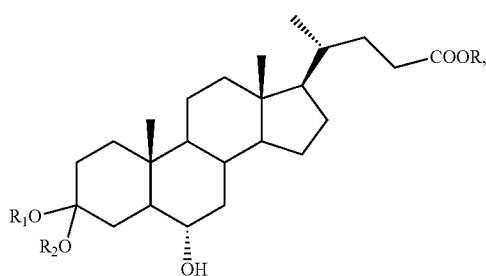

wherein $R_1$ and $R_2$ are as defined in claim 5 and R is as defined above;

c) oxidation of the hydroxyl group in position C-6 of a compound of formula (V), and optional saponification of the ester group, to obtain a compound of formula (VI).

8. The process according to claim 7, wherein a compound of formula (III) is prepared by protecting the carboxylic acid group of hyodeoxycholic acid of formula (II)

(II)

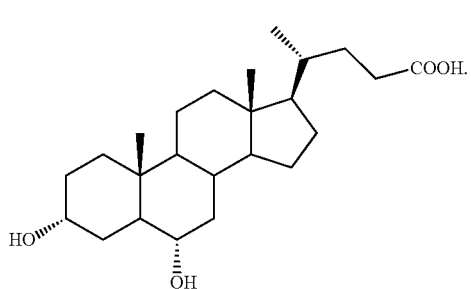

9. The process according to claim 5 further comprising the following steps:

f) stereoselective allylic oxidation of a compound of formula (VII), as defined in claim 5 and wherein $R_b$ is $OR_1$ and $R_c$ is $OR_2$, and $R_1$ and $R_2$ are as defined in claim 5, to obtain a compound of formula (IX):

(IX)

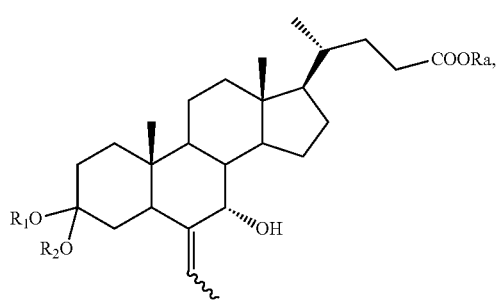

wherein $R_a$, $R_1$ and $R_2$ and the symbol ⁓ are as defined in claim 5;

g) removal of the protection at C-3 position of a compound of formula (IX) to obtain a compound of formula (X):

(X)

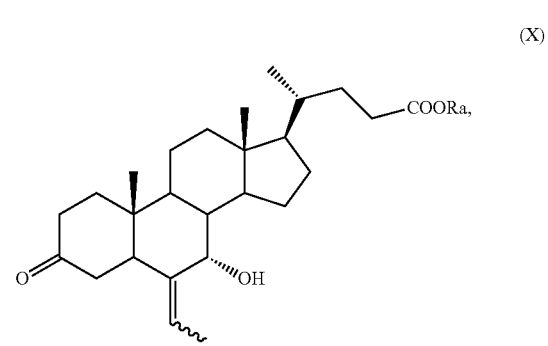

wherein $R_a$, and the symbol ⁓ are as defined in claim 5;

h) stereoselective reduction of the ketone group at C-3 position of a compound of formula (X) to provide a compound of formula (XI):

(XI)

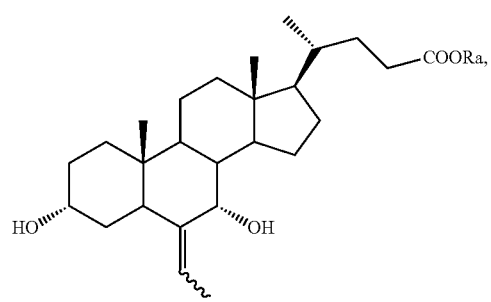

wherein $R_a$ and the symbol ⁓ are as defined in claim 5;

i) hydrogenation of a compound of formula (XI) to obtain a compound of formula (I);

or j) allylic oxidation in position C-7 of a compound of formula (VII), as defined in claim 5 and wherein $R_b$ is $OR_1$ and $R_c$ is $OR_2$, and $R_1$ and $R_2$ are as defined in claim 5, to obtain a compound of formula (XII):

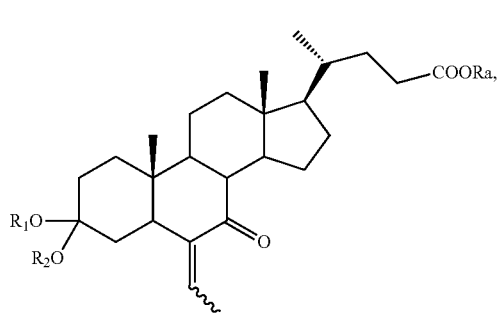

(XII)

wherein $R_a$, $R_1$ and $R_2$ and the symbol ⁓ are as defined in claim 5;

k) removal of the protection at C-3 position of a compound of formula (XII) to obtain a compound of formula (XIII):

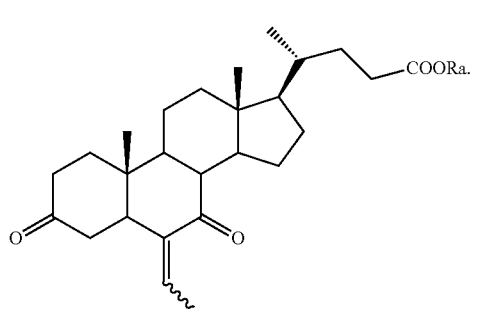

(XIII)

wherein $R_a$ and the symbol ⁓ are as defined in claim 5; and optionally its saponification;

l) hydrogenation of a compound of formula (XIII) to obtain a compound of formula (XIV):

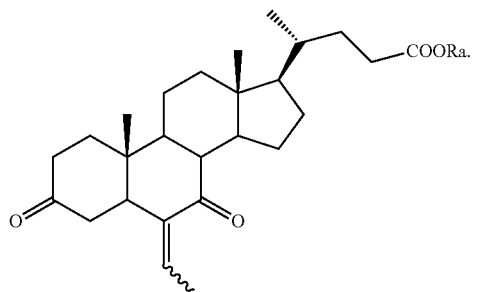

(XIV)

wherein $R_a$ and the symbol ⁓ are as defined in claim 5;

m) reduction of a compound of formula (XIV) to obtain a compound of formula (I);

or n) removal of the protection at C-3 position of a compound of formula (VII), as defined in claim 5 and wherein $R_b$ is $OR_1$ and $R_c$ is $OR_2$, and $R_1$ and $R_2$ are as defined in claim 5, to obtain a compound of formula (XV):

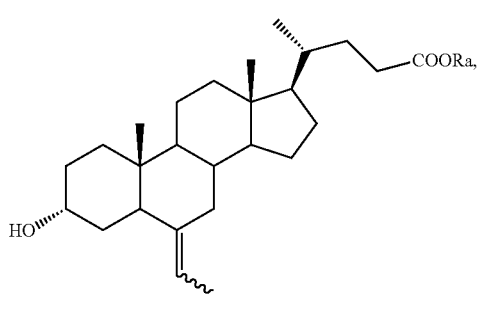

(XV)

wherein $R_a$ and the symbol ⁓ are as defined in claim 5;

o) stereoselective reduction of the ketone group at position C-3 of a compound of formula (XV) to obtain a compound of formula (XVI) and optional saponification of the ester function:

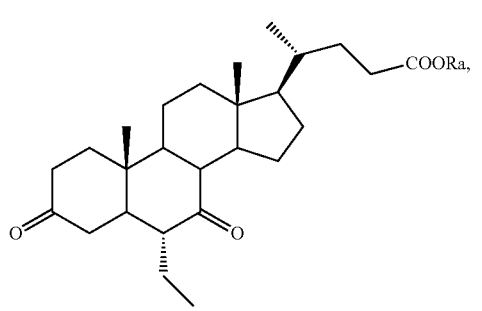

(XVI)

wherein $R_a$ and the symbol ⁓ are as defined in claim 5;

p) allylic oxidation in position C-7 of a compound of formula (XVI) and optional saponification of the ester function, to obtain a compound of formula (XI):

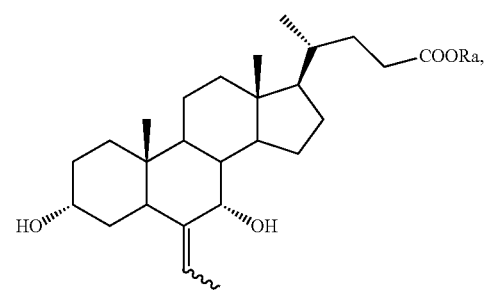

(XI)

wherein $R_a$ and the symbol ⁓ are as defined in claim 5;

q) hydrogenation of a compound of formula (XI) to obtain a compound of formula (I);

or r) protection of the hydroxyl group at C-3 position and allylic oxidation of position C-7 of a compound of formula (XVI), or allylic oxidation of position C-7 of a compound of formula (VII), and optional saponification of the ester function, to obtain a compound of formula (XVII),

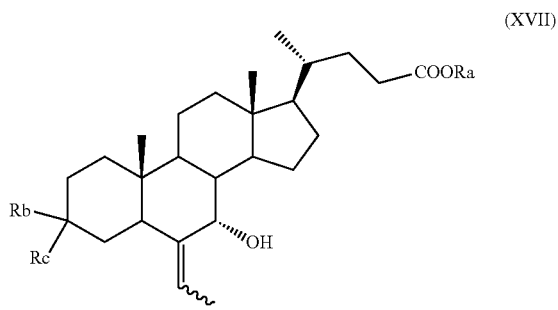

(XVII)

wherein the symbol ⌇, $R_a$, $R_b$, $R_c$ are as defined in claim 5;

s) oxidation of the hydroxyl group in position C-7 to the keto group and the removal of the protection at C-3 of a compound of formula (XVII) to obtain a compound of formula (XVIII):

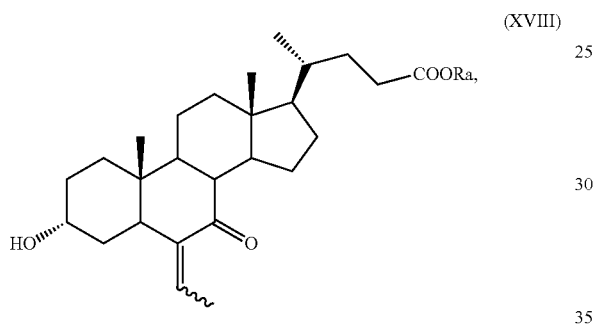

(XVIII)

wherein $R_a$ and the symbol ⌇ are as defined in claim 5;

t) hydrogenation and reduction of a compound of formula (XVIII) to obtain a compound of formula (I).

10. The process according to claim 6 further comprising the following steps n) removal of protection at position C-3 of a compound of formula (VIIa), as defined in claim 8 and wherein $R_b$ is $OR_1$ and $R_c$ is $OR_2$, and $R_1$ and $R_2$ are as defined in claim 6, to obtain a compound of formula (XVa):

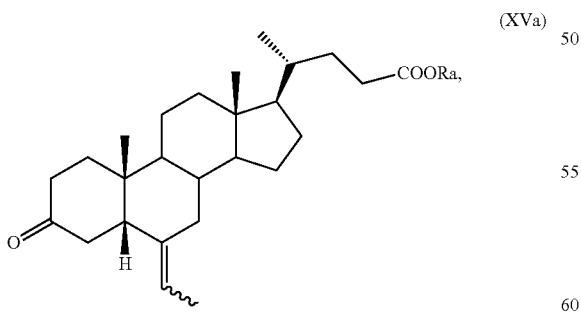

(XVa)

wherein $R_a$ and the symbol ⌇ are as defined in claim 6;

o) stereoselective reduction of the ketone group at position C-3 of a compound of formula (XVa) to obtain a compound of formula (XVIa) and optional saponification of the ester function:

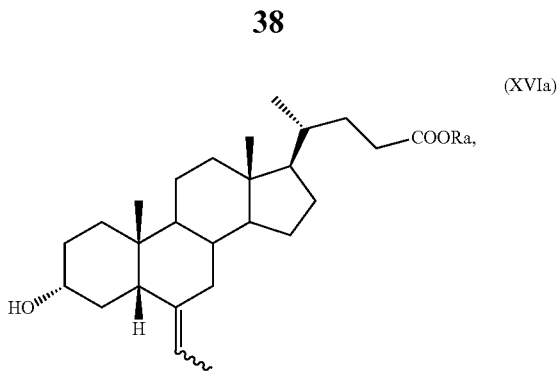

(XVIa)

wherein $R_a$ and the symbol ⌇ are as defined in claim 6;

p) allylic oxidation in position C-7 of a compound of formula (XVIa) and optional saponification of the ester function, to obtain a compound of formula (XIa):

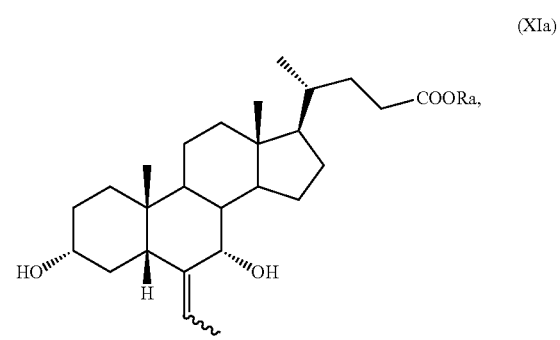

(XIa)

wherein $R_a$ and the symbol ⌇ are as defined in claim 6;

q) hydrogenation of a compound of formula (XIa) to obtain a compound of formula (Ia);

or r) protection of the hydroxyl group at C-3 position and allylic oxidation of position C-7 of a compound of formula (XVIa), or allylic oxidation of position C-7 of a compound of formula (VIIa), and optional saponification of the ester function, to obtain a compound of formula (XVIIa),

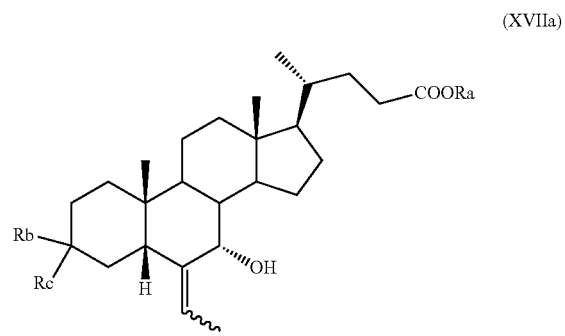

(XVIIa)

wherein the symbol ⌇, $R_a$, $R_b$, $R_c$ are as defined in claim 6;

s) oxidation of the hydroxyl group in position C-7 to the keto group and the removal of the protection at C-3 of a compound of formula (XVIIa) to obtain a compound of formula (XVIIIa):

(XVIIIa)

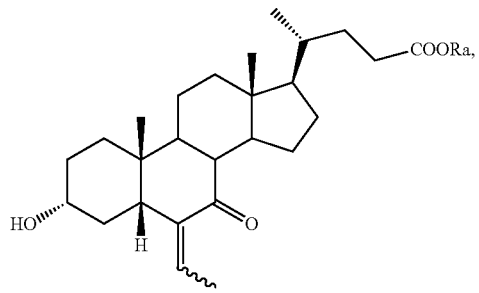

wherein R$_a$ and the symbol ⌇ are as defined in claim 6;

t) hydrogenation and reduction of a compound of formula (XVIIIa) to obtain a compound of formula (Ia).

11. The process according to claim 4, wherein the ketone obtained in step I) is a compound of formula (VI)

(VI)

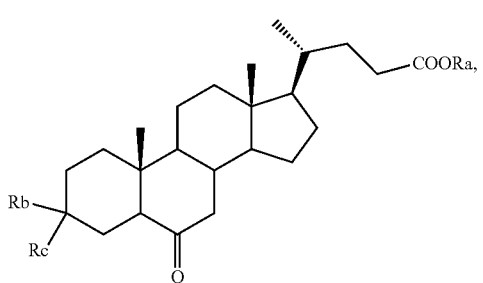

wherein R$_a$ is hydrogen or an optionally substituted linear or branched C$_1$-C$_6$ alkyl group, or an optionally substituted aryl;

R$_b$ is hydrogen and R$_c$ is OH or O-PG, wherein PG is an alcohol protecting group; or R$_b$ is OR$_1$ and R$_c$ is OR$_2$;

wherein each of R$_1$ and R$_2$, which are the same or different, is a C$_1$-C$_6$ alkyl group, or R$_1$ and R$_2$ taken together form a —(CH$_2$)$_n$— chain, wherein n is 2 or 3.

12. The process according to claim 11, wherein the ketone of formula (VI) as defined in claim 11 is reacted with a compound of formula (VIII)

(VIII)

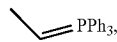

wherein Ph is phenyl,
providing a compound of formula (VII)

(VII)

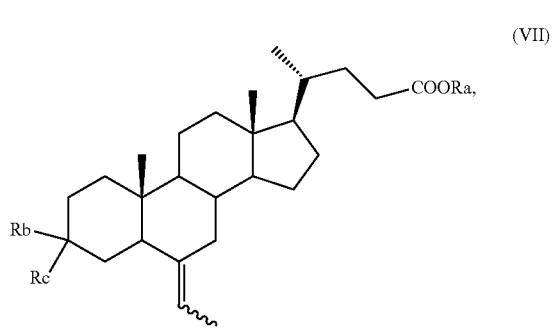

wherein R$_a$, R$_b$ and R$_c$ are as defined above
the symbol ⌇ indicates that the absolute configuration of the double bond can be (E) or (Z) or a mixture thereof; and
wherein the H-5 proton is either in configuration 5α or 5β, or a mixture thereof.

13. The process according to claim 12, comprising crystallizing the compound of formula (VII) as defined in claim 12 providing a compound of formula (VIIa):

(VIIa)

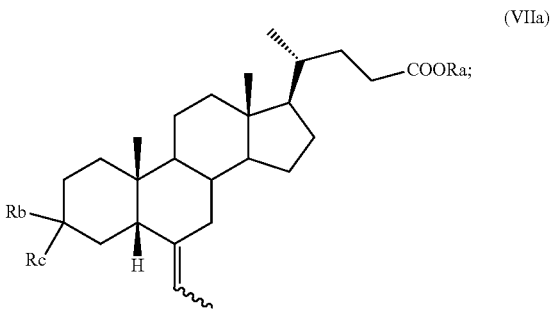

wherein the symbol ⌇, R$_a$, R$_b$ and R$_c$ are as defined in claim 12 and the proton H-5 of the compound of formula (VIIa) is in configuration 5β.

* * * * *